United States Patent
Botto et al.

(10) Patent No.: US 7,066,900 B2
(45) Date of Patent: Jun. 27, 2006

(54) REMOVAL OF METABOLIC COMPONENTS FROM BLOOD

(75) Inventors: Steven Anthony Botto, Rydalmere (AU); Philip John Roeth, Castle Hill (AU); Ellie Louise Faramus, Newport (AU); Chenicheri Hariharan Nair, Old Greenwich, CT (US)

(73) Assignee: Life Therapeutics, Frenchs Forest (AU)

( * ) Notice: Subject to any disclaimer, the term of this patent is extended or adjusted under 35 U.S.C. 154(b) by 492 days.

(21) Appl. No.: 10/234,423

(22) Filed: Sep. 4, 2002

(65) Prior Publication Data

US 2003/0187380 A1 Oct. 2, 2003

Related U.S. Application Data

(63) Continuation-in-part of application No. 09/470,822, filed on Dec. 23, 1999, now Pat. No. 6,855,121.

(30) Foreign Application Priority Data

Dec. 23, 1998 (AU) .................................. PP7908
Sep. 4, 2001 (AU) .................................. PR7485

(51) Int. Cl.
*A61M 37/00* (2006.01)
*B01D 61/00* (2006.01)
*B01D 35/06* (2006.01)
*C02F 1/44* (2006.01)
*C25B 15/00* (2006.01)

(52) U.S. Cl. .............. 604/6.08; 604/5.01; 604/4.01; 604/6.13; 210/748; 210/645; 210/195.2; 210/321.6; 210/902; 210/905; 204/450; 204/520; 204/527; 204/542; 204/627; 204/630

(58) Field of Classification Search ............... 604/4.01, 604/6.01, 5.01–5.04, 6.04, 6.08, 28, 6.09, 604/29, 6.11, 6.16; 422/44–48, 101; 128/898; 204/155–156, 450, 518, 520, 543, 627; 210/645–647, 210/650–652, 748, 767, 790–793, 194, 195.2, 210/196, 222, 223, 321.6, 321.71, 321.72, 210/321.75, 321.84, 322, 323.1, 902, 903, 210/905
See application file for complete search history.

(56) References Cited

U.S. PATENT DOCUMENTS

| | | | |
|---|---|---|---|
| 4,276,140 A | 6/1981 | Jain ........................... 204/180 |
| 5,437,774 A * | 8/1995 | Laustsen ..................... 204/518 |
| 6,969,453 B1 * | 11/2005 | Ogle et al. .................. 204/456 |
| 2005/0167270 A1 * | 8/2005 | Vigh et al. .................. 204/518 |
| 2005/0284762 A1 * | 12/2005 | Astorga-Wells et al. .... 204/451 |

OTHER PUBLICATIONS

Nitto Electric Ind KK, "Blood Treatment appts.—comprises plasma sepn. appts. with blood inflow circuit, electrophoresis appts. and blood return circuit", Derwent Abstract Accession No. 87-252867/36, JP 62172965 A, Jul. 29, 1987.

* cited by examiner

*Primary Examiner*—Patricia Bianco
(74) *Attorney, Agent, or Firm*—Cooley Godward LLP

(57) ABSTRACT

An electrophoresis system for removing or reducing concentration of a metabolic component from blood or plasma of a subject is provided. A method for removing or reducing concentration or amount of a metabolic component in blood or plasma of a subject is also provided. The system and method include use of a set of ion permeable barriers and the application of an electrical potential across these barriers to selectively remove metabolic components from blood or plasma.

30 Claims, 19 Drawing Sheets

REMOVAL OF METABOLIC COMPONENTS FROM BLOOD

CROSS-REFERENCE TO RELATED APPLICATIONS

This application claims priority from Australian provisional application no. PR7485 filed Sep. 4, 2001 and is a continuation-in-part of U.S. patent application Ser. No. 09/470,822, filed Dec. 23, 1999 which claims priority from Australian provisional application no. PP7908 filed Dec. 23, 1998.

FIELD

The present application relates to removal of an unwanted component or components, particularly metabolic products, from blood or plasma using membrane-based electrophoresis.

BACKGROUND

In renal failure, loss of kidney function results in uremic syndrome, characterized by the accumulation of salts, water and toxic breakdown products of protein metabolism in the blood. There are approximately one million people worldwide with chronic kidney failure, with an annual growth rate of around 9%. Current therapies are based on conduction (diffusion—passive transport of solutes from blood to dialysate across a dialysis membrane), convection (ultrafiltration—simultaneous transport of solvent and solute from the blood compartment to the dialysate compartment across a dialysis membrane) and adsorption (protein adsorption depends on how hydrophobic the membranes are) strategies. Dialysis is a therapy which eliminates the toxic wastes from the body due to kidney failure. There are two main types of dialysis: hemodialysis and peritoneal dialysis. The majority (85%) of end stage renal disease (ESRD) patients are treated using a technique called hemodialysis which uses a passive diffusion strategy.

Hemodialysis entails the re-routing of blood from the body to a filter made of plastic capillaries, for example, passing blood through an artificial kidney, where uremic toxins, such as salts and urea (low molecular weight molecules), diffuse across a semipermeable membrane into isotonic dialysate, resulting in reduced toxin concentration in the blood. The blood is purified when the waste products diffuse from the blood across the membrane of these tiny capillaries. The blood is then returned to the body, usually via a vein in the arm. However, as toxic molecules increase in size, their ability to be removed by diffusion decreases. Typically, only 10% to 40% of larger molecules, called middle molecular weight molecules, are removed during a dialysis session. Consequently, these toxins reach abnormally high levels and begin to damage the body over time. The inefficient removal of uremic toxins, such as middle molecule toxins (e.g. β-2-microglobulin) and phosphate represent significant limitations of current renal dialysis technology. Currently, to achieve minimum adequate removal of urernic toxins, manufactures and nephrologists are attempting to increase the surface area of the artificial kidneys and prolong the patient treatment times. However, as blood priming is required for dialysis, there is a limit to the surface area of an artificial kidney. The limit will be reached when the blood priming volume (which goes to waste) exceeds the human blood regeneration time. Also, increasing therapy times reduces the quality of life of a patient and increases the medical and ancillary staff requirements. Often, patients suffer from side effects, or morbidity, due to the inability of the hemodialysis procedure to completely replace the function of a normal living kidney.

In peritoneal dialysis, the body's own membrane is used as a filter, and the fluid drained in and out of the abdomen replaces the kidneys in getting rid of toxins. However, this technique may result in peritonitis and membrane failure.

In healthy individuals, the kidney functions to remove excess water, salts and small proteins from the blood circulation. Nitrogenous wastes removed by the kidney include urea, the final metabolic destiny of excess dietary nitrogen, creatinine which is produced during muscle activity, and uric acid (an endpoint product of nucleotide metabolism). Current renal dialysis technology relies on equilibrium/diffusion principles and transmembrane pressure to remove nitrogenous wastes, salts and excess water from the bloodstream of patients experiencing chronic or acute renal failure. Current dialysis technologies suffer from sub-optimal biocompatibility of the dialysis membranes used, the inadequacy of existing technology in the removal of some solutes such as phosphates, and poor removal of low molecular weight proteins such as beta-2 microglobulin.

Beta-2-microglobulin (β2m) associated ainyloidosis affects long term dialysis patients. Under normal physiological conditions, free circulating β2m can be found in plasma at low concentrations (1–3 mg/L). However, this level can be up to fifty times higher in long term dialysis patients. In healthy individuals, glomerular filtration and catabolism in the proximal renal tubule effectively remove β2m. The impairment of renal function often leads to the retention of β2m and subsequent increase in its circulating concentration. Further, current dialysis treatments are unable to efficiently remove β2m at a sufficient rate leading to its accumulation and deposition as part of amyloid fibrils in various niusculoskeletal structures. These amyloid deposits are predominantly osteoarticular and are associated with various clinical manifestations such as carpal tunnel syndrome, joint pain and stiffliess, bone cysts, pathological fracture and soft tissue masses. The clinical problems associated with β32m amyloidosis constitute a major cause of morbidity in long term dialysis patients.

Beta-2 microglobulin is an 11.9 kDa non-glycosylated protein comprising a polypeptide chain of 99 amino acid residues. It is encoded by a single gene on chromosome 15, and is synthesized with an 18 residue signal peptide. 132m is ubiquitously expressed on the surface of all nucleated cells where it functions as the light chain of HLA class I molecule via a non-covalent association with the heavy chain and is required for transport and expression of the complex at the cell surface. It has also been shown to have amino acid sequence homology with the constant domain of $IgG_{(CH3)}$ and the alpha-3 domain of the heavy chain HLA class I. Several isoforms of β2m have been described, the native β2m and more acidic variants which are found in long term dialysis patients, possessing isoelectric points of 5.7 and 4.8 to 5.3 respectively.

Existing renal dialysis modalities employ diffusive and/or convective means to remove contaminating molecules from blood. Blood is passed through a disposable cartridge where the blood travels in one direction and dialysate, separated from the blood stream by a semi-permeable membrane, flows in the opposing direction.

Diffusive removal means that when blood is dialysed against a physiological dialysate solution, contaminant molecules present in blood, but absent from the dialysate, diffuse down their concentration gradient, out of the blood stream and into the dialysate stream. This is the mode of contaminant removal employed in 'conventional renal dialysis'. Dialysis of this type is usually adequate for the removal of low molecular weight solutes, but is entirely inadequate for the removal of larger blood components or contaminants like β2 microglobulin.

Convective removal means that blood is processed over a membrane at a pressure sufficient to force fluid (but not cells) through the membrane. This is referred to as hemofiltration, and allows removal of blood contaminants that are carried out by the bulk flow of fluid from the blood. Some fluid removal is the balanced by the infusion of a substitution solution into the patient to maintain correct body fluid balance.

Diffusive and convective means of solute removal may be combined in the dialysis mode known as hemodiafiltration, in which blood, maintained at a relatively high pressure, is dialysed against a dialysate solution maintained at a lower pressure. Solutes are able to diffuse across the semi-permeable membrane, while the simultaneous bulk fluid removal from blood, induced by transmembrane pressure, adds to the rate of solute removal. In HDF, a substitution solution is also used to maintain fluid balance, and may be added to blood before or after processing in the dialysis cartridge.

Gradiflow™ is a membrane-based preparative electrophoresis technology developed by Gradipore Limited (Australia) in which separations are achieved using the dual strategy of molecular charge and size. The distinguishing features of this technology are a set of hydrogel membranes and the application of an electrical potential across these membranes to drive a separation. The use of these features allows the selective removal of contaminants or a product from complex starting materials, which has been demonstrated in a number of protein purifications.

SUMMARY

The present application relates to various methods and apparatus for removing unwanted components from blood or plasma using membrane-based electrophoresis.

In one aspect, a system for removing or reducing concentration of a metabolic component from blood or plasma includes a first and second ion-permeable barrier, each having a defined pore size, which is disposed in an electric field area. A treatment chamber is formed between the first and second ion-permeable barrier. A structure cools the blood or plasma. Another structure provides dialysate to a cathode zone and an anode zone. A transporting device provides blood or plasma to the treatment chamber. Upon application of the electric potential, a metabolic component from the blood or plasma moves through at least one barrier into one of the cathode or anode zones.

In another aspect, a method for removing or reducing concentration of a metabolic component in blood or plasma includes placing blood or plasma from the subject in a treatment chamber of an electrophoresis system. Applying an electric potential between the cathode and anode causes movement of a metabolic component from the blood or plasma though a barrier into at least one of the electrode zones. This application step is maintained until the desired amount of removal of the metabolic component from the blood or plasma is achieved. The blood or plasma in the treatment chamber is returned to the subject. This method does not result in heating the blood or plasma above physiological temperature.

These and other features of the claims will be appreciated from review of the following detailed description of the application along with the accompanying figures.

DETAILED DESCRIPTION

In one aspect, the present claims provide an electrophoresis system for removing or reducing the concentration of a metabolic component or components from blood or plasma of a subject, comprising:

(a) a first ion-permeable barrier having a defined pore size and pore size distribution disposed in an electric field area;

(b) a second ion-permeable barrier having a defined pore size and pore size distribution disposed between the cathode zone and the first barrier so as to define a treatment chamber therebetween;

(c) means adapted for cooling blood or plasma from the subject;

(d) means adapted to provide dialysate to the cathode zone and an anode zone; and (e) means adapted to provide blood or plasma from the subject to the treatment chamber wherein, upon application of the electric potential, a metabolic component from the blood or plasma is caused to move through at least one barrier into at least one of the cathode or anode zones.

Figure 1:
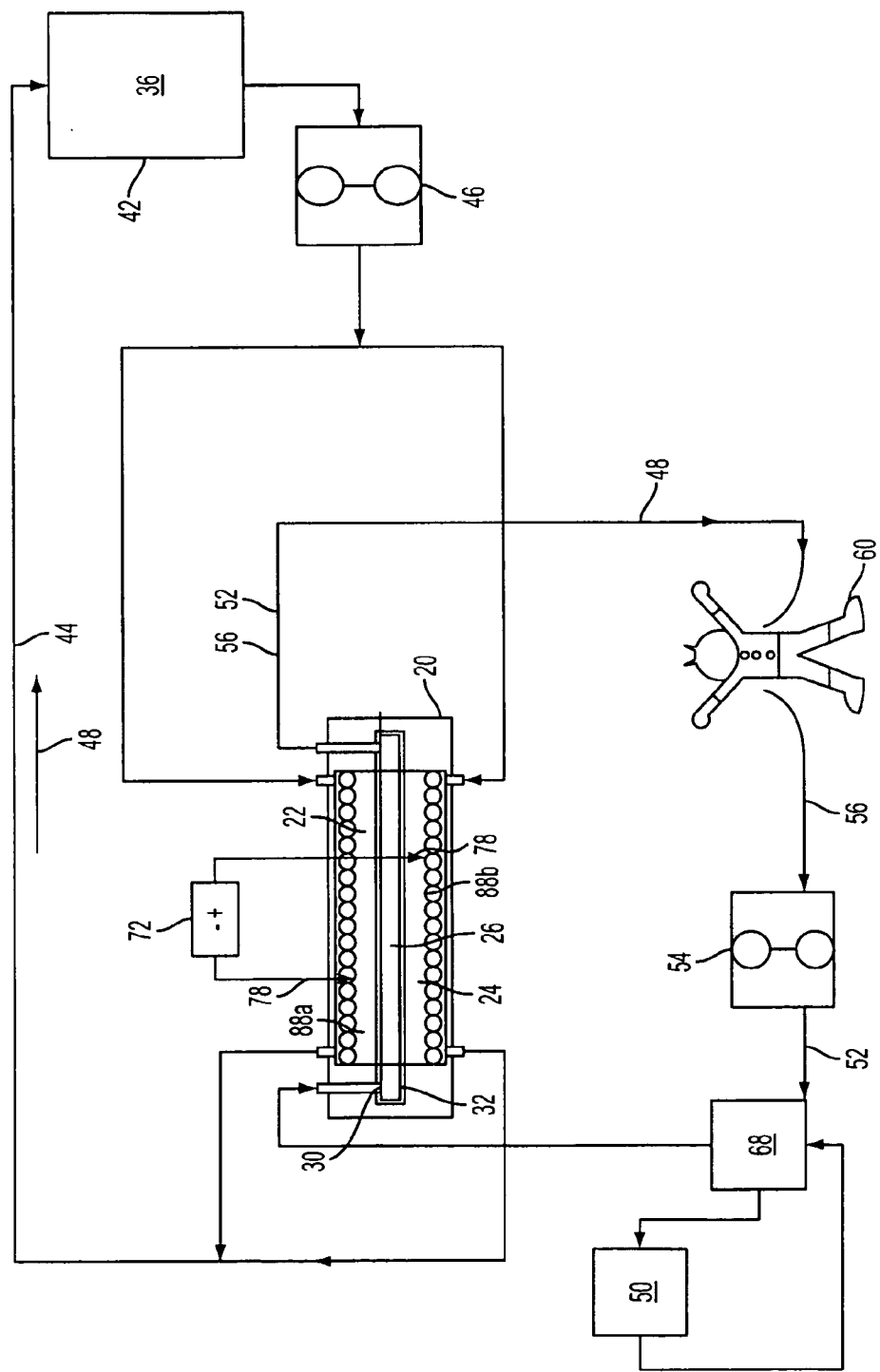
FIG. 1 shows a schematic of configuration of a membrane-based electrophoresis system according to the present claims.

A schematic diagram of one embodiment of an electrophoresis system 10 utilizing a separation unit 20 is shown in FIG. 1. In this purely illustrative example, two electrode zones (cathode zone 22, anode zone 24) are connected to an anolyte flow circuit. The flow circuit 40 comprises an anolyte reservoir 42, anolyte tubing 44, and anolyte pump 46.

Sample flow circuit 48 contains cooling means 50, tubing 52 and pump 54. Sample 56 flows from a subject 50 to cooling means in the form of a heat exchanger 60 through tubing 52 to pump 54, then through inlet into treatment chamber 26. In one embodiment, the flow directions of the anolyte 36 and sample 56 in the treatment chamber 26 are opposite. Sample 56 exits separation unit 20 at outlet and flows through tubing 52, returning to subject 50 through tubing 52. In another embodiment, the flow directions of sample 56 in the treatment chamber and anolyte 36 are the same.

Preferably, all tubing 44 and 52 is peristaltic tubing that is autoclavable, chemically resistant, and biologically inert. One such tubing is Masterflex® C-FLEX® 50 A tubing. Also, pumps 46 and 54 are preferably peristaltic pumps that are not in contact with anolyte 36 and sample 56. In the presently preferred embodiment, heat exchanger 68 is constructed from stainless steel, although other materials known in the art are suitably used. Preferably, heat exchanger 68 is autoclavable, chemically resistant, biologically inert and capable of facilitating heat exchange of the blood or plasma sample.

In one embodiment, when the patient is connected to the system 10, sample flow circuit 48 and anolyte flow circuit 40 are completely enclosed to prevent contamination or cross-contamination.

The separation unit 20 further comprises electrodes 88a and 88b. Preferably, the respective electrodes are located in the cathode and anode zones and are separated from the treatment chamber by ion-permeable barriers.

Electrodes 88a and 88b are suitably standard electrodes or preferably are formed from platinum coated titanium expanded mesh, providing favourable mechanical properties, even distribution of the electric field, long service life and cost efficiency. Electrodes 88a and 88b are preferably located relatively close to ion-permeable barriers 30 and 32 providing better utilization of the applied potential and diminished heat generation. A distance of about 0.1 to 6 mm has been found to be suitable for the system. For larger versions, the distance will depend on the number and type of ion-permeable barriers, and the size and volume of the electrode zones and treatment chamber. Preferred distances would be in the order of about 0.1 mm to about 10 mm.

Separation unit 20 also preferably comprises electrode connectors 78 that are used for connecting separation unit 20 to power supply 72. Preferably, power supply 72 is external to separation unit 20, however, separation unit 20 is configurable to accept internal power supply 72. Electrode connectors 78 are preferably autoclavable.

Movement of metabolic components from blood or plasma sample is achieved when an electric potential is applied to separation unit 20. Selection of the electric field strength (potential) varies depending on the separation. Typically, the electric field strength varies between 1 V/cm to about 500 V/cm, preferably between 10 V/cm to 80 V/cm and leads to currents of up to about 1 A. It is preferable to maintain the total power consumption of the unit at the minimum, commensurable with the desired separation and production rate.

In another embodiment, the system further includes:
(f) means adapted to return treated blood or plasma to the subject.

The metabolic component can be any unwanted metabolic component in blood or plasma such as small compounds and middle weight proteins. In one embodiment, the metabolic components are solutes including phosphates, nitrogenous wastes like urea and uric acid, or macromolecules including beta-2 microglobulin and other unwanted proteins including autoantibodies.

Although conventional dialysis procedures currently do not remove phosphate and beta-2-microglobulin, one embodiment is particularly suitable as an adjunct to standard dialysis treatments.

The subject can be a patient with renal abnormalities which requires renal dialysis, or a patient with liver abnormalities, for example.

The cathode zone and the anode zone are supplied with suitable dialysate or buffer solutions by any suitable pumping means. The blood or plasma is supplied to the treatment chamber by any suitable pumping means. Suitable pumping means are readily ascertainable to the skilled practitioner.

The first and second barriers can have the same defined pore size and pore size distribution or different defined pore size and pore size distribution. In one embodiment, the barriers are hydrogel membranes formed from polyacrylamide or any other suitable polymer. For use in treating blood or plasma, the membranes may have a defined pore size and pore size distribution which will not allow the movement of serum albumin. Typically, the barriers or membranes have a nominal molecular mass cut-off of less than about 60 kDa.

The selection of the molecular mass cut-off of the barriers or membranes will depend on the sample being processed and the metabolic components to be removed. It will be appreciated, however, that other membrane chemistries or constituents can be used for the present claims.

There may be situations where two or more treatment chambers are required. If so, then the system according to the present claims may further include a third ion-permeable barrier having a defined pore size and pore size distribution disposed in the electric field area forming a second treatment chamber. Similarly a plurality of treatment chambers may be required. If so, then the system according to the present claims may further include a plurality of ion-permeable barriers having defined pore sizes and pore size distributions disposed in the electric field area forming a plurality of treatment chambers.

In one preferred form, the barriers or membranes forming the treatment chamber are provided as a cartridge or cassette positioned between the electrode zones of the systems. Preferably, the cartridge or cassette is removable from an electrophoresis apparatus adapted to contain or receive the cartridge. The electrodes can be housed in the electrophoresis apparatus or positioned in the cartridge. The cartridge can be disposable or adapted for reuse. As different membranes may be required for different treatments, combinations can be supplied, in sterile form if necessary, for single use. Alternatively, the cartridge can be disassembled and fresh barriers or membranes inserted.

Preferably, the electrode zones and the treatment chamber are configured to allow flow of the respective dialysate and blood/plasma forming streams. In this form, large blood or plasma volumes can be processed quickly and efficiently.

Preferably, the dialysate is moved or recirculated through the electrode zones from a reservoir by a suitable pumping means. In a preferred embodiment, peristaltic pumps are used as the pumping means for moving the dialysate and blood/plasma.

In some embodiments, the cooling means is selected from gas, liquid or solid heat transfer system or systems, cooled fluid jacket heat exchanger, or peltier cooler. More preferably, the cooling means is a gas, liquid or solid heat transfer system or systems.

The blood/plasma can also be recirculated from the subject to the system and returned to the subject over a period of time until the amount unwanted metabolic products is reduced.

The system is typically built in modular form from components that are biocompatible and are easily disassembled for cleaning, disinfection or sterilization.

In use, blood or plasma is removed from the subject, passed through the cooling means to reduce the temperature of the blood or plasma, and passed into the treatment chamber. Dialysate is provided to the electrode zones, an electric potential is applied to the electric field area causing at least one metabolic component in the blood or plasma to move to through at least one barrier or membrane into the respective cathode zone or anode zone. After treatment, the blood or plasma is returned to the subject. The blood or plasma may be continuously treated via recirculation from the patient through the system or batch processed by holding the blood or plasma in the treatment chamber.

The system according to the present claims is suitable for renal dialysis of animals, particularly humans.

The components of systems have been found to be biocompatible and do not adversely affect blood components when put back into patients after dialysis.

In another aspect, the present claims provide a method for removing or reducing the concentration or amount of a metabolic component in blood or plasma of a subject, the method comprising:
(a) placing blood or plasma from the subject in a treatment chamber of an electrophoresis system according to the first aspect of the present claims;
(b) applying an electric potential between the two electrodes causing movement of a metabolic component from the blood or plasma through a membrane into at least one of the electrode zones;
(c) maintaining step (b) until the desired amount of removal of the metabolic component from the blood or plasma is achieved; and
(d) returning the treated blood or plasma in the treatment chamber to the subject, wherein the method substantially does not result in the blood or plasma being heated above physiological temperature of about 37° C.

In one embodiment, the blood or plasma is passed through the cooling means prior to being passed to the treatment chamber. One embodiment cools the blood or plasma prior to being passed to the treatment chamber. In one example, the blood or plasma is preferably cooled to a temperature below physiological temperature (about 37° C.) by an amount of the heating that is expected to occur when the blood or plasma in treated in the treatment chamber. As some heating occurs during electrophoresis which can cause unwanted hemolysis of blood or destruction or inactivation of blood or plasma components, treatment should not result in the blood or plasma being substantially heated above physiological temperature (about 37° C.). Cooling the blood or plasma prior to treatment overcomes any problems with over heating the blood or plasma during treatment.

In another embodiment, the blood or plasma is passed through the cooling means of the electrophoresis system according to the first aspect of the present claims to reduce the temperature of the blood or plasma prior to being passed to the treatment chamber of the electrophoresis system. This step assists in preventing the blood or plasma being heated above physiological temperature of about 37° C. During electrophoresis in the chamber, the blood and plasma can be warmed up to the desired temperature before being returned to the subject.

In another embodiment, the subject is a renal dialysis patient or a liver failure patient. In one example, the blood or plasma is preferably recirculated between the subject and the treatment chamber.

The barriers can have a molecular mass cut-off close to the apparent molecular mass of metabolic component. It will be appreciated, however, that the barrier may have any required molecular mass cut-off depending on the application.

In one example, during electrophoresis, cellular and biomolecular components of the blood or plasma are substantially retained in the treatment chamber, or if entering a barrier, being substantially prevented from entering the electrode chambers.

In another example, the metabolic components are solutes including but not limited to phosphates, nitrogenous wastes like urea and uric acid, or middle weight proteins including, for example, beta-2 microglobulin and other unwanted proteins including autoantibodies.

In one embodiment, the barriers are membranes have a molecular mass cut-off of between about 3 and about 60 kDa to ensure that larger proteins such as albumin are not lost from the blood or plasma. It will be appreciated, however, that other size membranes may be applicable, depending on the treatment process required. A number of different barriers or membranes may also be used in a desired or useful configuration.

The electric potential applied during the method should preferably not substantially adversely affect the cells or proteins present in blood or plasma. An electric potential of up to about 100 volts has been found to be suitable. It will be appreciated, however, that other voltages may be used.

Flow rate of the blood/plasma sample or dialysate can influence the separation of the metabolic components. Rates of 20 ml/min have been found to be suitable. However, increasing the scale of the separation also increases the flow rates. It would be expected that flow rates between 200–800 ml/min would be achievable in a scaled-up electrophoresis system. Depending upon the application of the electrophoresis system (adjunct or stand alone unit), flow rates between 20–1000 ml/min would be anticipated.

Selection or application of the voltage and/or current applied varies depending on the application. Typically up to about 100 volts can used, but choice and variation of voltage will depend on the configuration of the apparatus, dialysate and the sample to be treated. Importantly, the voltage used should not result in 'over heating' the blood or plasma resulting in hemolysis or inactivation or destruction of blood or plasma components. The use of an optimized cooling system will enable the electrical potential applied across the system to be increased. Scaling-up the electrophoresis system will also result in increasing the electrical potential applied across the system.

Optionally, the electric potential may be periodically stopped and/or reversed to cause movement of a constituent having entered a barrier or membrane to move back into the sample in the chamber, while substantially not causing any constituents that have passed completely through a barrier or membrane to pass back through the barrier or membrane.

Reversal of the electric potential is an option but another alternative is a resting period. Resting (a period without an electric potential being applied) is an optional step that can replace or be included before or after an optional electrical potential reversal. This resting technique can often be practised for specific applications as an alternative or adjunct to reversing the potential.

In one form, at least one blood component has undergone treatment such as diffusive hemodialysis, convective hemodialysis, hemofiltration, hemodiafiltration, or combinations prior to, subsequent to, or concurrently with step (a).

In another aspect, the present claims provide a method for renal dialysis of a subject, the method comprising carrying out hemodialysis on blood or plasma of the subject followed by treating the blood or plasma of the subject according to methods described in the present claims.

As conventional hemodialysis often fails to remove certain metabolic components from the blood of renal patients which can result in the build-up of these components, a treatment process selectively remove these components.

In one embodiment, the method comprises:
(a) carrying out hemodialysis on blood or plasma of a patient;
(b) placing blood or plasma from the hemodialysed patient in a treatment chamber of an electrophoresis system according to the first aspect of the present claims;
(c) maintaining step (b) until the desired amount of removal of the metabolic component from the blood or plasma is achieved; and
(d) returning the treated blood or plasma in the treatment chamber to the subject, wherein the method substantially does not result in the blood or plasma being heated above physiological temperature of about 37° C.

For example, the components can be phosphates or proteins such as beta-2 microglobulin or autoantibodies. It will be appreciated, however, that other unwanted metabolic components can also be removed in this process.

In another aspect, the present claims relates to use of the system according to the first aspect of the present claims in the dialysis of renal patents.

In another aspect, one embodiment relates to a combination of an electrophoresis system adapted to assist in the dialysis of patients together with an artificial kidney, a plasma separating device, or an apheresis device.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present claims. It is not to be taken as an admission that any or all of these matters form part of the prior art base or were common general knowledge in the field relevant before the priority date of each claim of this application.

To assist in understanding the present application, the following examples are included and describe the results of a series of experiments. The following examples relating to this application should not be construed to specifically limit the application or such variations of the application, now known or later developed, which fall within the scope of the claims as described and claimed herein.

Abbreviations and Nomenclature

In this specification, abbreviations are used to describe particular compartments or processes associated with membrane-based electrophoresis and its uses in blood treatment, as well as metabolic parameters tested. Below is a list of the abbreviations, with a brief description.

A-G ratio—Albumin:Globulin ratio.
AST—Aminotransferase.
BF200—General Gradiflow™ laboratory electrophoresis model produced by Gradipore Limited (Australia).
Buffer stream or Dialysate stream—The stream circulating on the outside of the membranes. Dialysate usually in the form of Fresenius was placed in this stream.
C3a—Complement factor C3a. A protein that takes part in the complement cascade to finally produce membrane attack complex during an immune response.
Cartridge configuration 1 stream (dialysis)—A membrane cartridge constructed using one restriction membrane and one separation membrane which formed one stream (S1). The cartridge was typically configured with the restriction membrane on top and the separation membrane on the bottom, resulting in the sample stream being loaded into S1. The convention for describing the cartridge configuration was from top to bottom; top restriction-separation eg 100–100 kDa molecular mass cut-off.
Cartridge configuration 2 streams—A membrane cartridge constructed using one separation membrane between two restriction membranes forming two streams (S1 and S2). The convention for describing the cartridge configuration was from top to bottom; top restriction-separation—bottom restriction eg 3-100-3 kDa molecular mass cut-off.
C-bilirubin—Conjugated bilirubin.
CK—Creatine Kinase.
Consort power supply—Power supply capable of reaching 300V/2A/150W (typically limited to 250V/IA/150W in protein separations) in low conductivity environments.
DF100—Membrane-based electrophoresis model termed Dialysis Flow 100.
ESRD—End Stage Renal Disease.
Gamma GT—Gamma Glutamyl transferase.
GLDH—Glutamate Dehydrogenase.
Hb—Hemaglobin.
MCH—Mean Cell Hb.
MCHC—Mean Cell Hb Concentration.
MCV—Mean Cell Volume.
PCV—Packed Cell Volume.
RBC—Red blood cells.
RDW—RBC distribution width.
RS power supply—Power supply capable of operating at a maximum of 63.3V/3A in high conductivity environments.
S1—Stream 1, or a first interstitial volume, of an electrophoresis system.
S2—Stream 2, or a second interstitial volume, of an electrophoresis system.
T-bilirubin—Total bilirubin.
WCC—White Cell Count.

Experimental Design

In current renal dialysis therapies, phosphate and problematic middle molecules are not adequately removed. In a renal dialysis setting, the system and methods according to the present claim's combined characteristics of protein removal and electrolyte dialysis has significant potential in the treatment of renally compromised patients. As the electrophoresis system and methods use an electrical potential to drive separations, molecules with a large charge:mass ratio, such as phosphate, were removed very quickly. Middle molecule toxins, which tend to be proteins with a molecular weight less than albumin, have a specific charge at a particular pH. By using the charge on a protein, and the molecular weight cut off of the membrane, reduction of middle molecule proteins are achieved.

The initial evaluation of membrane-based electrophoresis as shown in FIG. 1 ("electrophoresis system") in a renal dialysis setting determined whether uremic toxins could be removed from a starting material. The investigation of nitrogenous waste removal was initially conducted using a BF200 model Gradiflow™ using small volume (12 ml) starting samples. For all runs, either an acetate-bicarbonate hemodialysis dialysate (Fresenius) or lactate peritoneal dialysate (Baxter) was used as a buffer solution. Commercial dialysates were used as they had been identified to be physiologically compatible in renal dialysis treatments and also provided an easier means of using the electrophoresis system as an adjunct to current dialysis therapies. The small volume nitrogenous waste removal experiments initially used a 15V potential in the BF200 to produce molecule movement profiles. As some of the molecules tested had a low charge to mass ratio and hence motility, a 63.3V potential was used to increase the molecule transfer rate.

The small volume (12 ml) nitrogenous waste removal experiments involved evaluating whether The electrophoresis system could remove spiked uremic toxins (urea, uric acid, creatinine, phosphate and β-2-microglobulin) from buffer. The buffer was then replaced with normal and spiked plasma, blood and renal patient dialysate. The renal patient dialysate was used as a alternative source for middle molecule toxin β-2-microglobulin reduction experiments.

Identifying that specific uremic toxins were removed when using the electrophoresis system from blood/plasma, resulted in determining whether the process was biocompatible. As literature reviews provided no clear indication as to whether polyacrylamide hydrogel membranes (information relating to the use of polyacrylamide-containing contact lens and dermal patches were identified, however the information was not relevant to blood contact biocompatibility) and an electrical potential were biocompatible, both were investigated. To make the biocompatibility data for a BF200 more relevant to a dialysis situation, the processing volume changed from 12 ml to 100 ml. Increasing the starting volume enable the electrophoresis system to treat a blood volume similar to that found in an average person. The biocompatibility parameters chosen to provide a preliminary overview of blood/hygrogel/electrical potential interaction were hemolysis, coagulation, complement and white cell pathways. The results from this study can be found in "Biocompatibility Aspects".

To reduce the amount of hemolysis produced by the BF200 and make the electrophoresis system more clinically applicable, a dialysis electrophoresis system was developed. The dialysis system was designated Dialysis Flow 100 (DF100—the differences between the BF200 and DF100 are described below). The DF100 reduced hemolysis and maintained the same biocompatibility aspects of the BF200.

To determine the parameters required for scaling the DF100 to treat a blood volume found in a human, several parameters were investigated. The parameters investigated were biocompatibility, electrical potential, buffer and electrolyte analysis, and larger volume uremic waste removal.

Identifying that the in vitro process was capable of removing uremic wastes and that the measured biocompatibility markers demonstrated no significant adverse effect, an animal study was conducted. The animal study established the in vivo biocompatibility of the claimed electrophoresis system in an ovine model. The results from the phase 1 animal study can be found below.

The results obtained from the animal study have identified that the electrophoresis system was capable of being used as a medical device.

Results

Nitrogenous/Uremic Waste Removal

This experiment established the electrophoresis system's ability to remove uremic wastes (urea, creatinine and uric acid) and phosphate from spiked buffer, plasma and whole blood.

Methods

Blood and plasma were obtained from healthy volunteers. One mg/ml Urea (60 Da), 0.1 mg/ml creatinine (113 Da, pKb 10.4), 0.25 mg/ml uric acid (168 Da, pKa 5.75) and 0.1 mg/ml phosphate were added to 12 ml samples of blood or plasma. This spiked blood or plasma was placed in S1 of the electrophoresis system BF200. Bicarbonate hemodialysis dialysate (Fresenius Medical Care South East Asia Pty Ltd, Smithfield NSW Australia) was used in the buffer stream. For these experiments, cartridges were assembled without a middle separation membrane to give one sample stream. A 15V potential was applied across a 25 kDa/25 kDa membrane cartridge. Samples were taken every 5 minutes for 1 hour and assayed for removal of urea, creatinine, uric acid and phosphate using standard clinical test kits (Trace Scientific Ltd, Melbourne Vic Australia). A 15V potential was chosen in order for a clear profile of molecule movement to be observed. Since most of these molecules have a high charge to mass ratio and hence motility, a higher voltage moved the molecules too quickly for a comparative profile to be established.

Plasma was obtained from renal dialysis patients with elevated levels of β2 microglobulin (12 kDa. pI 5.8). This plasma was placed in the S1 of the electrophoresis system BF200. Bicarbonate hemodialysis dialysate (Fresenius, Medical Care South East Asia Pty Ltd, Smithfield NSW Australia) was placed in the S2 and buffer stream. A 63V (RS power supply) potential was placed across a 3-200-3 kDa membrane arrangement in conventional configuration. Samples were taken from the S1 and S2 and assayed for removal of β2-microglobulin using Behring nephelometer 100 analyser and Dade Behring nephelometry reagents (Dade Behring, Germany). A 63V potential was used in order to enable movement of a protein. Due to a portein's lower charge to mass ratio than the molecules used above, a higher potential was required.

Results

Urea

Figure 2:
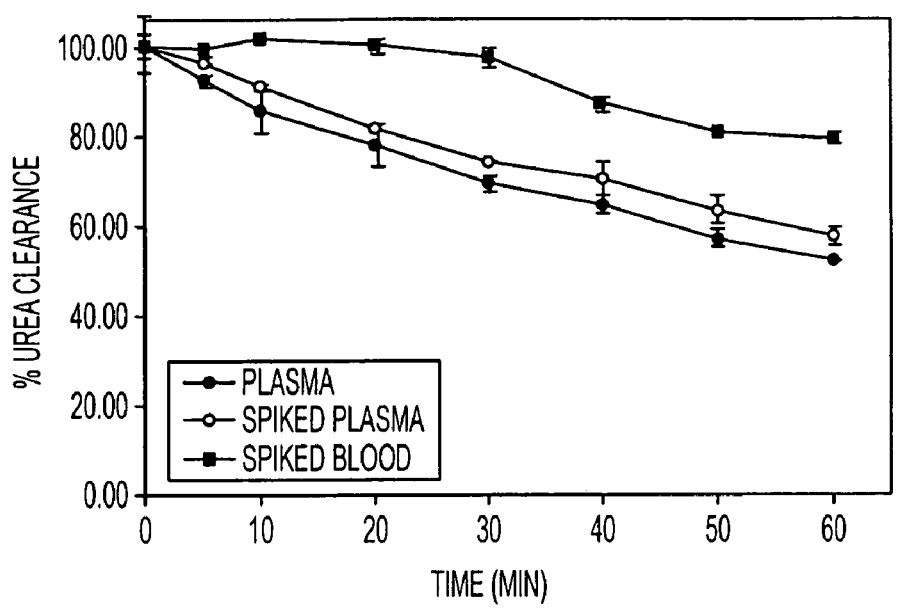
FIG. 2 shows urea removal from plasma, spiked blood and spiked plasma.

Urea, an uncharged molecule, was removed from plasma, spiked blood and spiked plasma by passive diffusion, same principle as hemodialysis. Plasma showed a clearance of 49% after 1 hour while the removal from spiked blood and spiked plasma was 21% and 43% respectively (FIG. 2).

Creatinine

Figure 3:
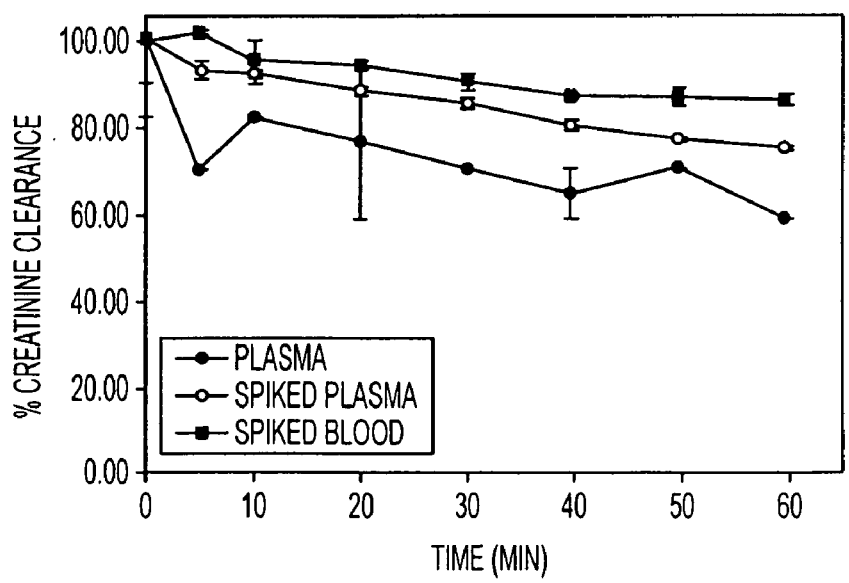
FIG. 3 shows creatinine removal from plasma, spiked blood and spiked plasma.

Creatinine carries a slight positive charge at physiological conditions resulting in voltage dependent removal. After 1 hour 41% of creatinine was removed from normal plasma samples with 14% and 25% removal obtained from spiked blood and spiked plasma respectively (FIG. 3).

Uric Acid

Figure 4:
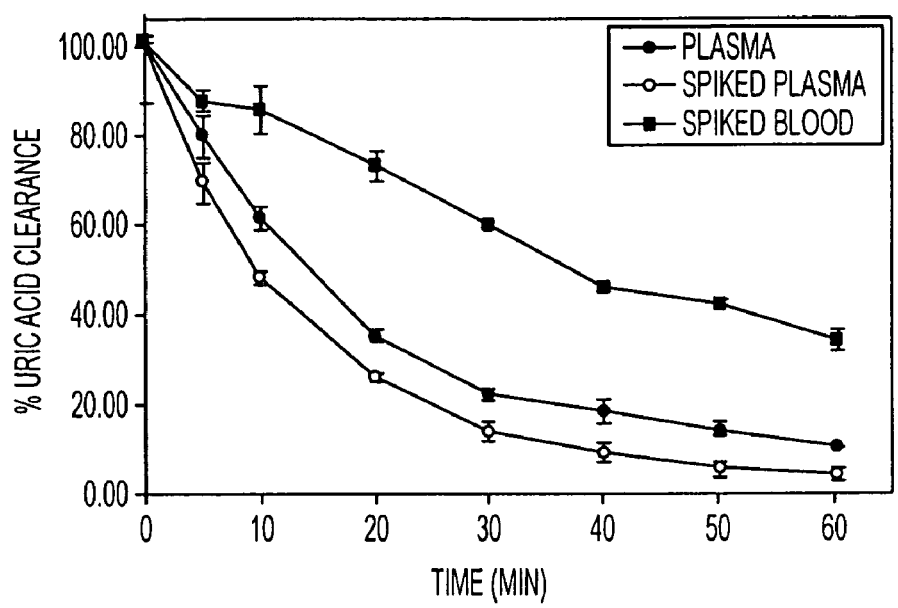
FIG. 4 shows uric acid removal from plasma, spiked blood and spiked plasma.

In a physiological environment, uric acid carries a negative charge, hence removal was also found to be dependent on voltage. After 1 hour 89% of the uric acid was cleared from normal plasma samples. The removal from spiked blood was 66% and 96% was cleared from spiked plasma (FIG. 4).

Phosphate

Figure 5:
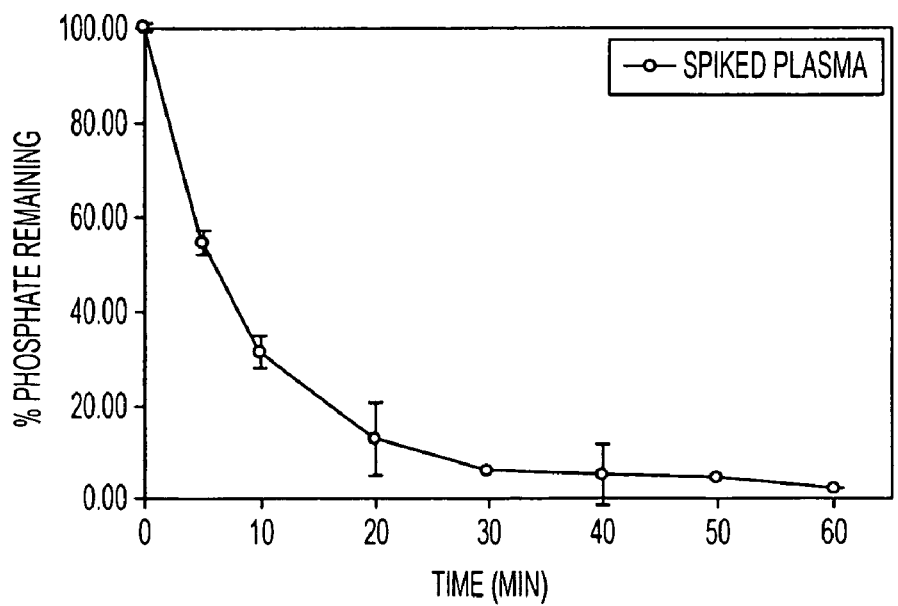
FIG. 5 shows phosphate removal from spiked plasma.

Phosphate also has a negative charge at pH 7.4, again leading to a voltage dependent removal rate. From spiked plasma, 98% of the starting phosphate concentration was removed after one hour (FIG. 5).

Conclusion

The electrophoresis system was capable of removing uremic toxins from small blood and plasma volumes. The removal of the uremic toxins by either passive diffusion or by a voltage dependant means suggested a roll for the electrophoresis system as a stand alone dialysis unit or an adjunct to existing dialysis technologies. The most significant benefit was observed in the removal of phosphate, a problematic molecule which requires constant control in dialysis patients.

β-2-microglobulin and Phosphate Removal

Spiked Buffer Experiments

This experiment established the movement of β-2-microglobulin and phosphate from spiked buffer.

Materials and Methods

Commercially available β-2-microglobulin (Research Diagnostcs, Inc) and phosphate were spiked into 20 ml stream 1 buffer (buffer+20 mg/ml dextran–blocking agent) to a final concentration of 0.1 mg/ml (3.23 mmol/l). Stream 2 had 10 ml buffer+dextran. Samples were taken from both streams 1 and 2 at times 0, 5, 10, 15, 20, 30, 45, 60 and 62 minutes. At 60 minutes, the voltage was switched off and the streams allowed to recirculate for 2 minutes prior to a final saimple being taken. Each experiment was perfonned in triplicate, with triplicate analysis of each time point sample.

Sample (300 μl) of a 20 mg/ml stock solution of β-2-microglobulin and 30 μL of a 200 mg/ml stock solution of phosphate were spiked into 60 ml of buffer to give final concentrations of 0.1 mg/ml.

Results

Figure 6:
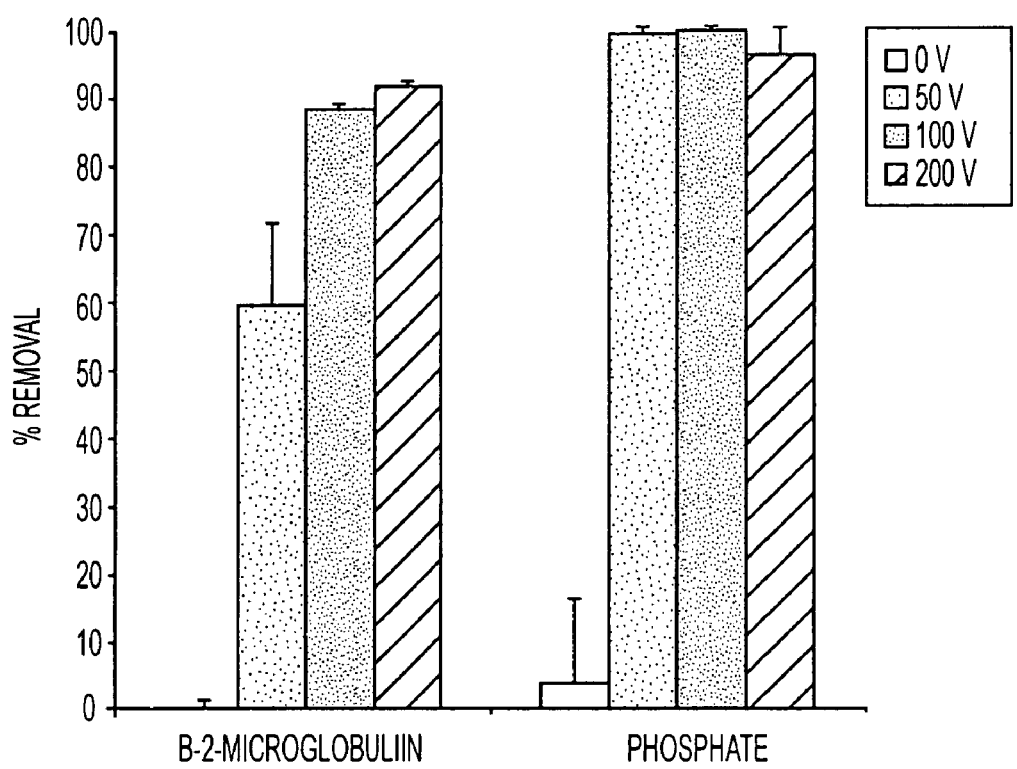
FIG. 6 shows effect of an electrical potential on the transfer of β-2-microglobulin and phosphate through a 50 kDa separation membrane using a Tris Borate buffer (pH 8.4)
Figure 7:
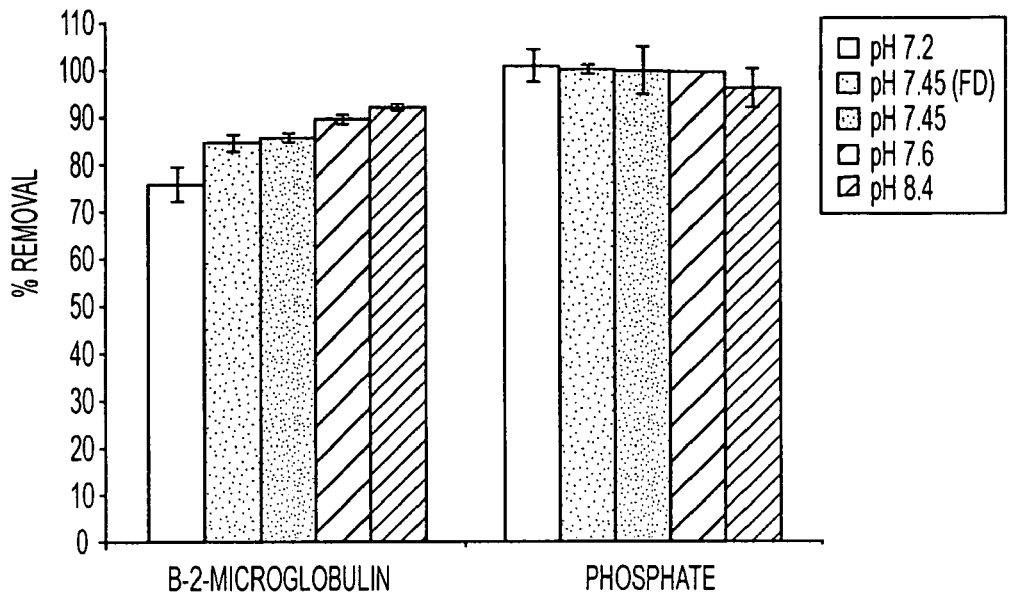
FIG. 7 shows effect of pH on the transfer of β2-microglobulin and phosphate through a 50 kDa separation membrane using a 200V potential.
Figure 8:
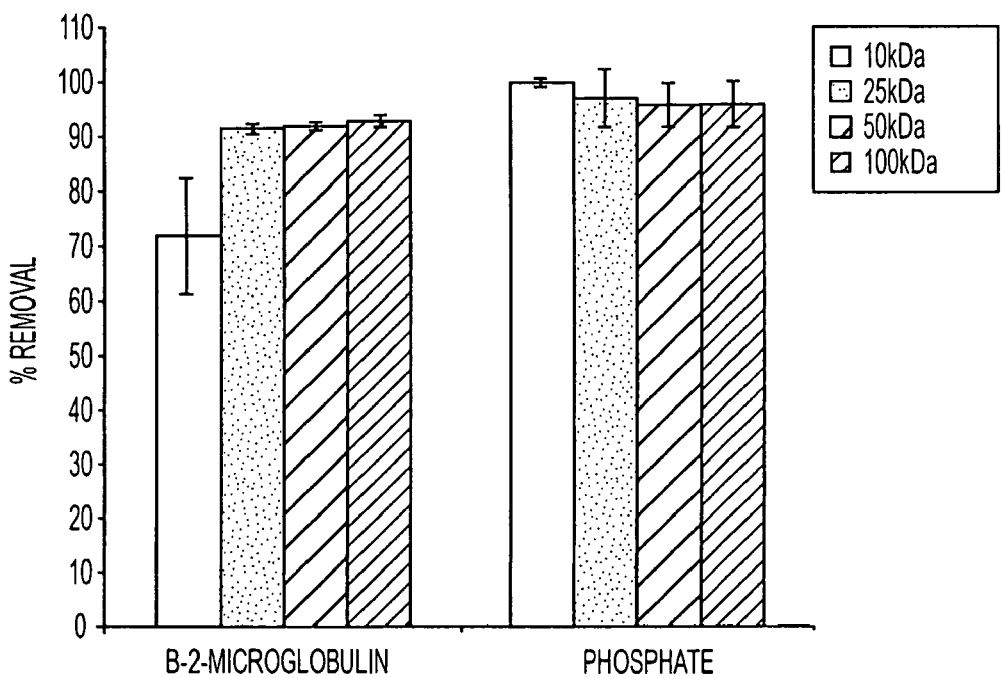
FIG. 8 shows effect of membrane pore size on the transfer of β-2-microglobulin and phosphate using a 200V potential.

The electrophoresis system moved both β-2-microglobulin and phosphate. The movement of phosphate was dependent upon the electrical potential, but independent of pH, ionic strength and membrane pore size (FIG. 6, FIG. 7 and FIG. 8). Movement of β-2-microglobulin however, was dependent upon the membrane pore size, pH, ionic strength and the applied electrical potential (FIG. 7).

When voltage was applied, >95% of phosphate was removed after 1 hour under all conditions when an electrical potential was applied. For β-2-microglobulin as the electrical potential was increased, the removal rate of β-2-microglobulin increase. The voltage dependant removal of β-2-microglobulin resulted in 60±12%, 88±1% and 92±1% removal with the application of 50V, 100V and 200V respectively after 1 hour (FIG. 6).

The removal rates of β-2-microglobulin increased under more basic conditions, with 90±1% of β-2-microglobulin removed Within 30 min at pH of 8.4 compared to 77±3% at pH 7.6 and 41±16% at pH 7.25. However, after 60 minutes >75.6% of β-2-microglobulin was removed in all pH conditions (FIG. 7).

The rate of β-2-microglobulin removal however, was dependent upon the membrane pore size. Results showed an increased removal of β-2-microglobulin from S1 of 76±10% to 93±1% when the membrane pore size was increased from 10 kDa to 100 kDa respectively (FIG. 8). There was no significant difference in the rate of transfer of β-2-microglobulin in with the 25 kDa, 50 kDa and 100 kDa membrane.

Spiked Blood and Plasma

This experiment investigated movement of β-2-microglobulin and phosphate from spiked blood and plasma.

Materials and Methods

Steam 1 contained 30 ml of fresh heparinized plasma or blood, from volunteers with normal kidney function. The blood and plasma in S1 were spiked with commercial β-2-microglobulin and phosphate to a final concentration of 0.1 mg/ml (3.23 mmol/L). Fifteen ml buffer plus 20 mg/ml dextran and 12 units/ml heparin was placed into S2. Samples were taken from both streams S1 and S2 at times 0, 5, 10, 15, 20, 30, 45, 60, 90, 120 and 122 minutes. At 120 minutes, a 63V electrical potential was switched off and the streams allowed to recirculate for 2 minutes prior to a final sample being taken. Each experiment was performed in duplicate, with triplicate analysis of each time point sample.

Sample (150 μl) of a 20mg/ml β-2-microglobulin stock and 15 μl of a 200 mg/ml stock of phosphate was spiked into 30 ml of blood or plasma to give a final β-2-microglobulin and phosphate concentration of 0.1 mg/ml.

An alternative source of β-2-microglobulin was from dialysis patients plasma. For these experiments S1 contained 30 ml of dialysis patient plasma was used. Fifteen ml buffer plus 20 mg/ml dextran and 12 units/ml heparin was placed into S2. Samples were taken from both streams S1 and S2 at times 0, 5, 10, 15, 20, 30, 45 and 60 minutes. At 60 minutes, a 63V electrical potential was switched off and the streams allowed to recirculate for 2 minutes prior to a final sample being taken. Each experiment was performed in duplicate, with triplicate analysis of each time point sample.

Results

Figure 9:
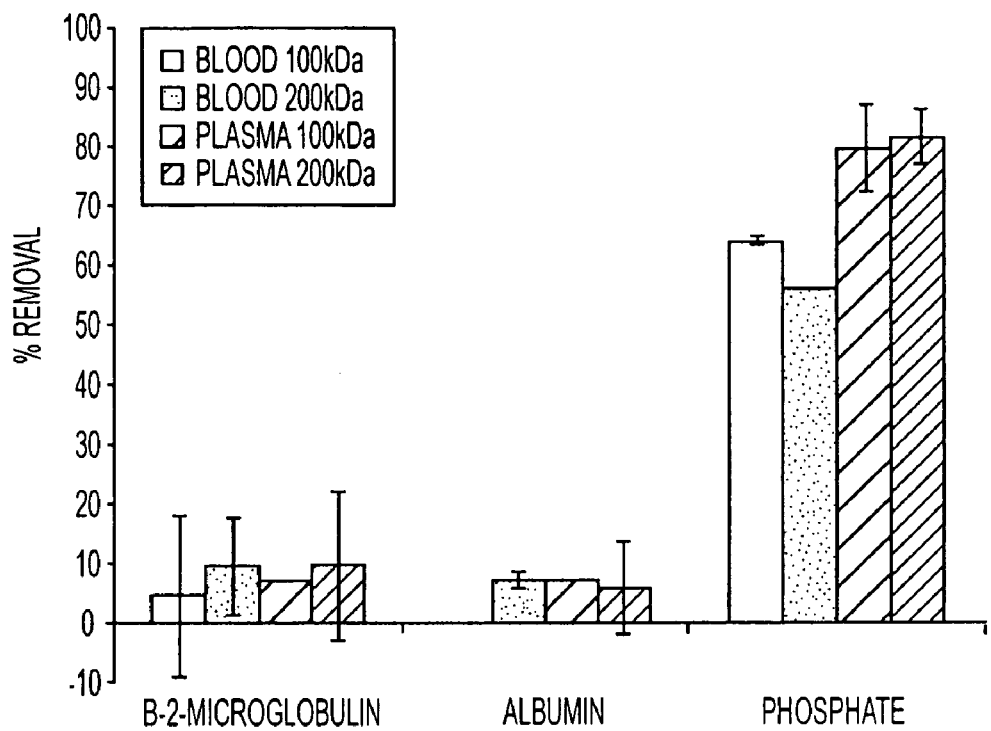
FIG. 9 shows movement of albumin, spiked β-2-microglobulin and phosphate from blood and plasma through a 100 kDa and 200 kDa separation membrane using a 63V potential.

The movement of spiked commercially available β-2-nucrogiobuhn and phosphate was retarded when spiked into heparinised blood or plasma compared to buffer. With a 63.3V potential, 5±14% and 10±8% of β-2-microglobulin was moved from blood in 120 minutes using a 100 kDa and 200 kDa membrane respectively. in comparison, 7% and 10±12% of β-2-microglobulin was moved in plasma under the same conditions (FIG. 9). The removal of β-2-microglobulin was comparable to albumin (5×times the size of β-2-microglobulin). A trend for improved removal of β-2-microglobulin with larger pore size membranes was observed. It should be noted thai albumin was removed as a second protein marker for separations. When the electrophoresis system is used as a medical device, a membrane with a pore size suitable to the application can be used. In the case of renal dialysis, a pore size which excludes the removal of albumin should be used.

In contrast, phosphate removal rates were higher, with 56–64% removal from spiked blood and 79–81% removal from spiked plasma (FIG. 9). The high percentage phosphate removal suggests a role for The electrophoresis system in the treatment of uremic patients.

Figure 10:
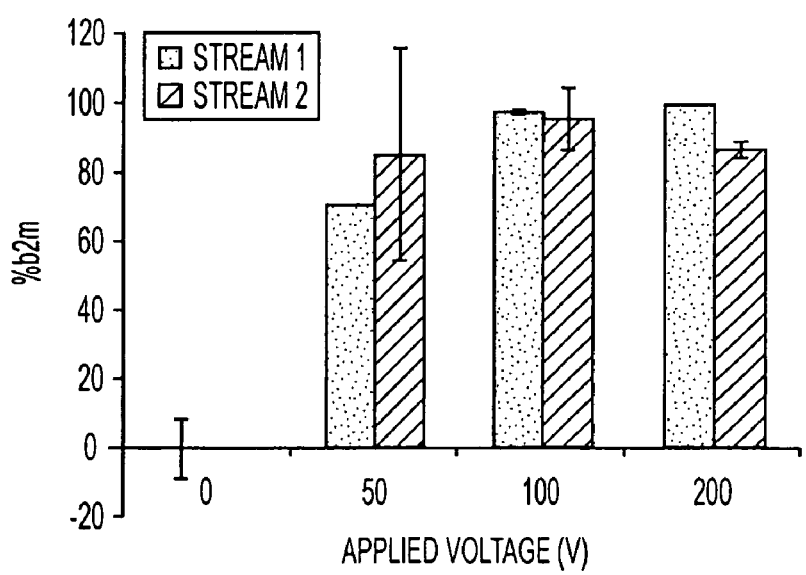
FIG. 10 shows beta-2 microglobulin removal was not due to membrane absorption. The lower series of bars (negative values) represent the percentage of beta-2 microglobulin removed from S1, while the upper bars (positive values) represent the percentage beta-2 microglobulin collected in S2, from S1, after the treatment.
Figure 11:
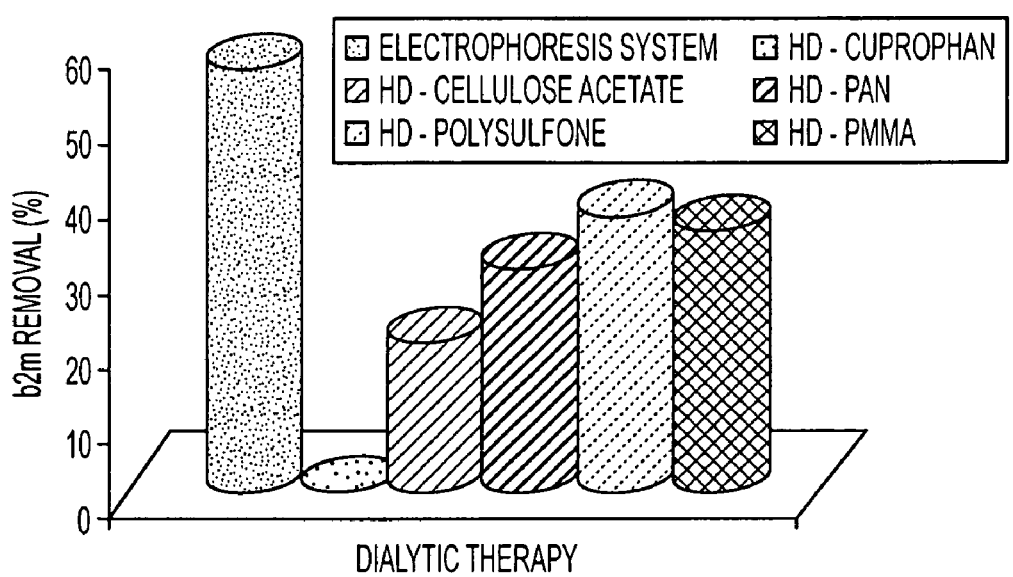
FIG. 11 shows comparison of performance of an electrophoresis system according to the present claims compared with current dialytic therapies in the removal of beta-2 microglobulin. The current dialysis therapies described in this graph are hemodialysis (HD) membranes composed of currently available commercial material (cuprophan, cellulose acetate, polyacrylonitrile (PAN), polysulphone and polymethylmethacrylate (PMMA))

The analysis of the movement of the β-2-microglobulin in dialysis patient plasma found that the removal of β-2-microglobulin with the electrophoresis system was not due to membrane absorption as found in current dialysis treatments (FIG. 10). This was concluded as 70–100% of β-2-microglobulin in S1 was transported, using the electrophoresis system, into S2. In FIG. 10, the lower bars indicate the percentage beta-2 microglobulin removal from S1 after the application of various voltages, ranging from 0 –200V. The upper bars indicate the percentage beta-2 microglobulin accumulation in S2, from S1 after the treatment. FIG. 11 illustrates the effective removal of beta-2 microglobulin in a 1 hour electrophoresis system treatment compared to current 4 hourly dialysis treatments. The results suggest that up to 60% of β-2-microglobulin was removed compared to approximately 0–40% removal by current hemodialysis treatments.

Biocompatibility Aspects

These experiments established biocompatibility of the hydrogel membranes and the electrical potential on cellular and biochemical components of human plasma and blood.

Methods

To investigate the biocompatibility whole blood and plasma were treated by the electrophoresis system and hemolysis, coagulation, complement and cellular activation were measured.

Blood and plasma were obtained from healthy volunteers and anticoagulated with either 0.38% sodium citrate or 12 units/ml heparin. Heparin was chosen as the anticoagulant where possible to represent as closely as possible the dialysis setting. For activated partial thromboplastin time (APTT) analysis, citrate was required as the anticoagulant in order for the assay to work.

Sample (100 ml) of the blood or plasma was recirculated in an electrophoresis system instrument configured for dialysis with a buffer steam of anticoagulated renal dialysis acetate/bicarbonate dialysate (Fresenius Medical Care). A 63V electrical potential was applied across blood/plasma and samples were taken at 0, 5, 10, 15, 20, 30, 45 and 60 minutes. At the specified time points, hemolysis, coagulation (activated partial thromboplastin time [APTT] and thrombin/antithrombin III complex [TAT]) and complement (C3a-des Arg) activation indices were measured to assess the biocompatibility of The electrophoresis system. The points on each graph represent mean values (n=3, x±SD).

Hemolysis

Hemolysis was measured using absorbances for hemoglobin at 540 nm. The amount of lysis was calculated as a percentage of total possible lysis and the difference between start and end or the various time points taken as the lysis occurring.

APTT (Activated Partial Thromboplastin Time)

APTT was analysed on the MLA Electra 800 automatic coagulometer using 0.2M calcium chloride from Gradipore and aPTT reagent from Dade Behring, Germany. TAT (thrombin anti-thrombin III complex). Formation of TAT was determined using Enzygnost TAT ELISA kits (Dade Behring, Germany). C3a (complement factor C3a). C3a was assayed using C3a-des arg ELISA kits from Quidel (California, USA) (supplied by Thermo Trace).

Platelet, Lymphocyte and Neutrophils Activation

Platelet and lymphocyte activation analysis of was performed by flow cytometry. Whole blood was processed in the electrophoresis system with and without the application of an electrical potential. For platelet activation, aliquots were taken and stained with CD61 PerCP and C62P PE monoclonal antibodies (Becton Dickinson, N.J., USA) and gated based on FSC/SSC- and CD61-staining properties. For lymphocytes, CD45 PerCP and CD62L PE monoclonal antibodies (Becton Dickinson, N.J., USA) were used as measures of activation. Lymphocytes were identified using a FSC/SSC/CD45 gate and analysed for CD62L expression. For neutrophils, CD45 PerCP and CD62L PE monoclonal antibodies (Becton Dickinson, N.J., USA) were used as measures of activation. Neutrophils were identified using a FSC/SSC/CD45 gate and analysed for CD62L expression.

Results

Hemolysis

Figure 12:
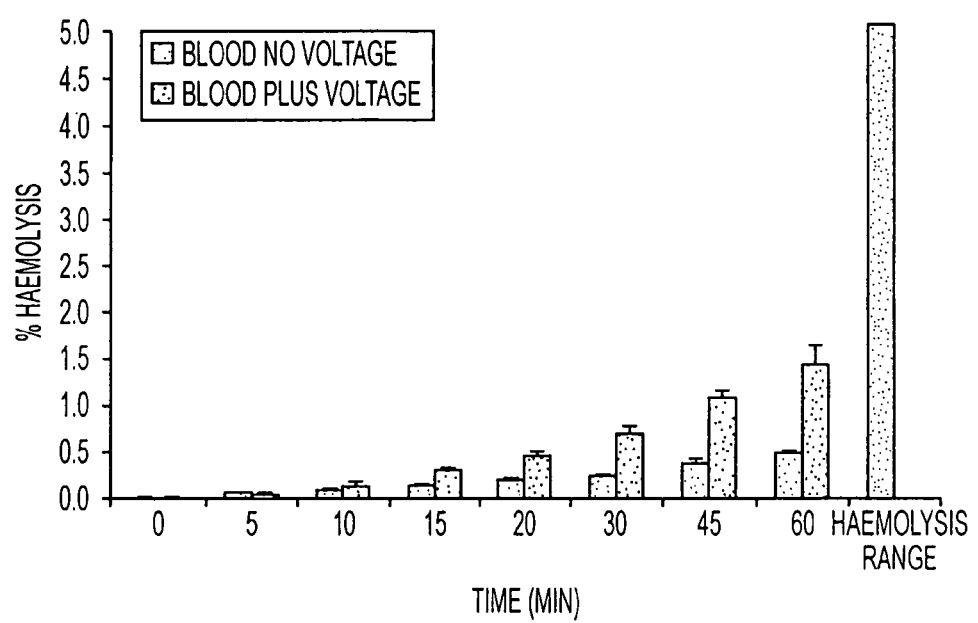
FIG. 12 shows effect of membrane based electrophoresis treatment on hemolysis.

The percentage hemolysis was measured to determine the effect of an electrical potential on anticoagulated whole blood. According to international standards, less than 5% hemolysis is acceptable for a medical device. The data demonstrated that with and without the application of an electrical potential, the observed hemolysis was within the acceptable range (FIG. 12). The results also indicated that an electrical potential increases hemolysis on recirculating blood. However, after a single pass through the electric field only 0.05% of red blood cells were lysed.

APTT

Figure 13:
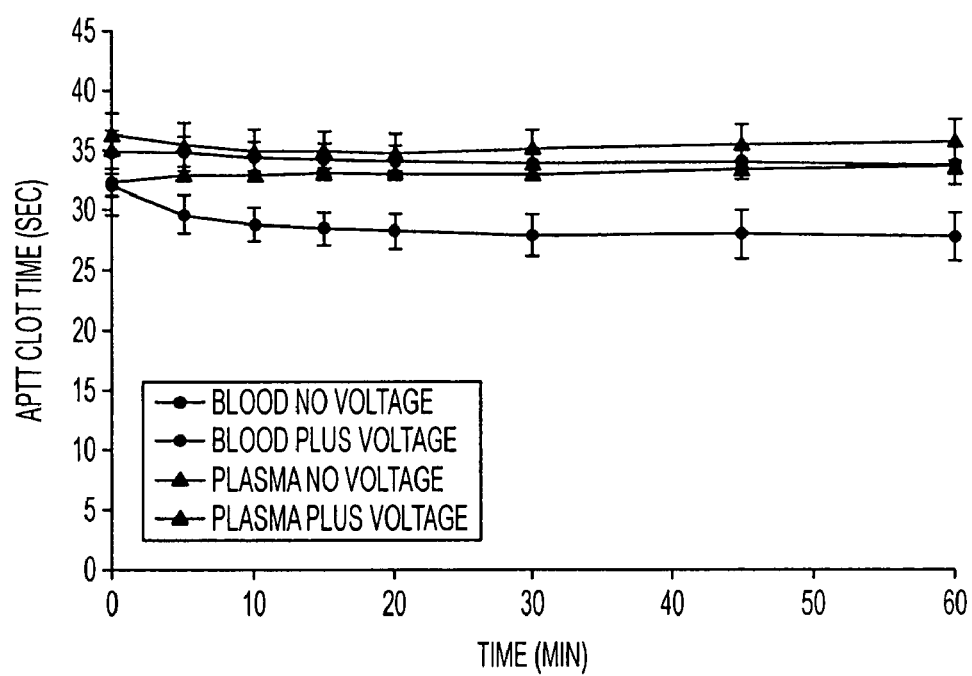
FIG. 13 shows effect of membrane based electrophoresis treatment on coagulation (APTT clot time)

These experiments measured the effect of an electrical potential on the coagulability of citrated whole blood and plasma. The results demonstrated that while a small decrease in APTT times was observed when an electrical potential was applied to either blood or plasma, this change was within the reference range of 25–39 seconds for healthy adults (FIG. 13). The change to the APTT times was less than 5 seconds, within a 10 second normal range associated with the control for healthy individuals.

TAT

Figure 14:
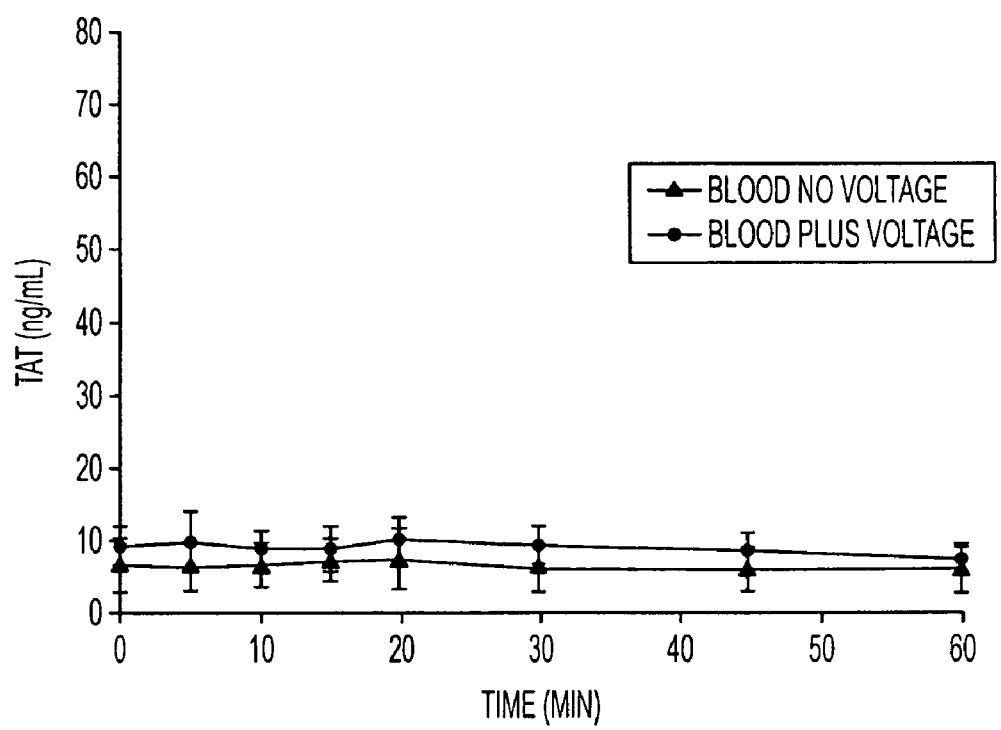
FIG. 14 shows effect of membrane based electrophoresis treatment on coagulation (TAT formation)

These results showed no TAT formation in heparinised blood, indicating that coagulation activation did not occur. Minor decreases of TAT complex concentration or dissociation were observed after 30 min and may be attributed to the movement of co-factors and small molecules away from the TAT complex (FIG. 14). Testing of polyacrylonitrile, acrylonitrile copolymer (AN69), cuprophan and polysulphone generated between 75–175 ng/ml TAT after 27 minutes, while polyacrylamide membranes with an applied electrical potential generated less than 3 ng/ml TAT from the control after 60 minutes.

C3a

Figure 15:
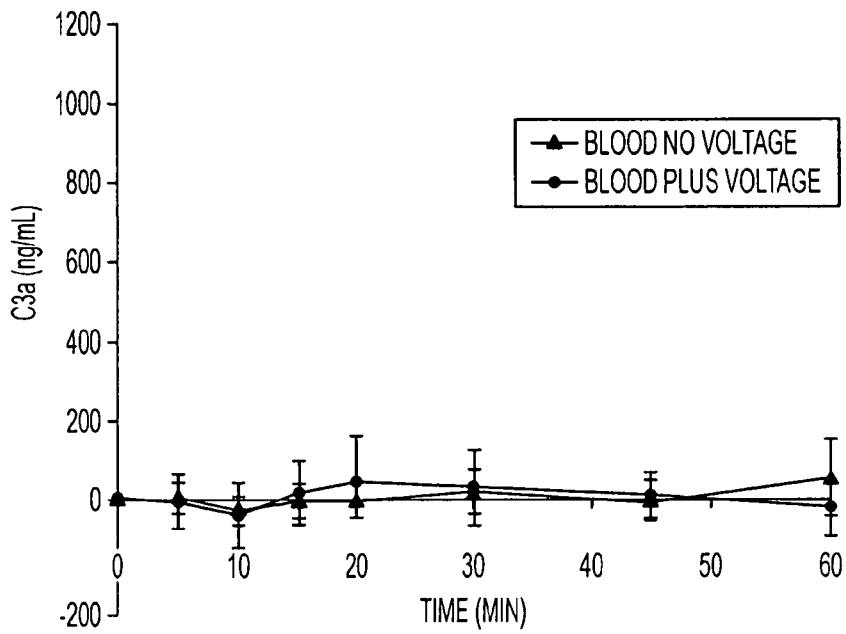
FIG. 15 shows effect of membrane based electrophoresis treatment on complement activation (C3a)

Measurements of C3a-desArg from heparinised blood indicated that polyacrylamide membranes and an electrical potential did not activate the complement pathway. In comparison testing of polyacrylonitrile, acrylonitrile copolymer (AN69), cuprophan and polysulphone between 80 ng/ml to in excess of 3000 ng/ml C3a were generated within 27 minutes from the baseline controls. With The electrophoresis system the largest increase in C3a levels was 44 ng/ml from baseline controls at 30 minutes and this was degraded or removed from the blood during the run (FIG. 15).

Platelets

Figure 16:
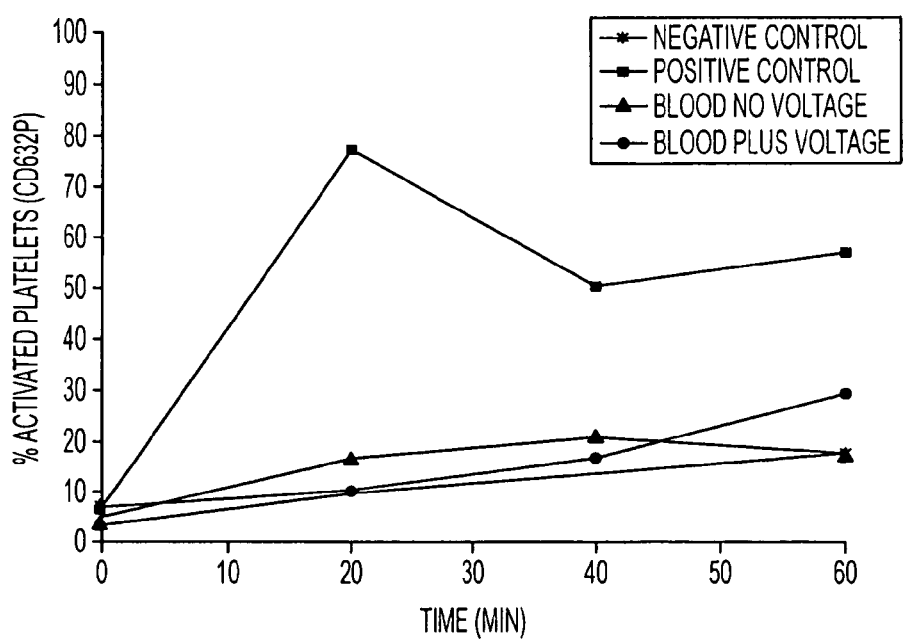
FIG. 16 shows effect of membrane based electrophoresis treatment on platelet activation in whole blood.

Whole blood was processed in The electrophoresis system with and without the application of an electrical potential. Aliquots were taken and stained with CD61 PerCP and C62P PE monoclonal antibodies. Platelets were gated based on FSC/SSC and CD61 staining properties. CD62P expression was measured as an indication of platelet activation. The application of an electric potential to whole blood did not cause significant platelet activation (FIG. 16). The positive control for platelet activation was treatment with ADP.

Lymphocytes

Figure 17:
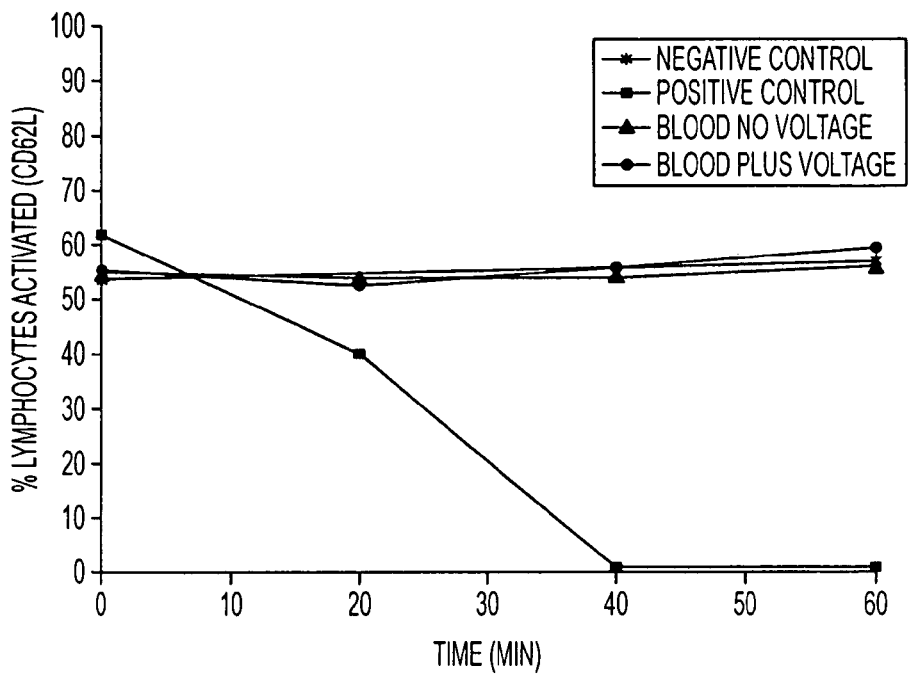
FIG. 17 shows effect of membrane based electrophoresis treatment on lymphocyte activation in whole blood.

Whole blood was treated as in FIG. 12. Aliquots were stained with CD45 PerCP and CD62L PE monoclonal antibodies. Lymphocytes were identified using a FSC/SSC/CD45 gate and analysed for CD62L expression. The positive control, treatment with phorbol myristate acetate (PMA), caused a rapid loss of surface CD62L. Treatment of whole blood with and without an electrical potential caused no significant change to lymphocyte CD62L expression (FIG. 17).

Neutrophils

Figure 18:
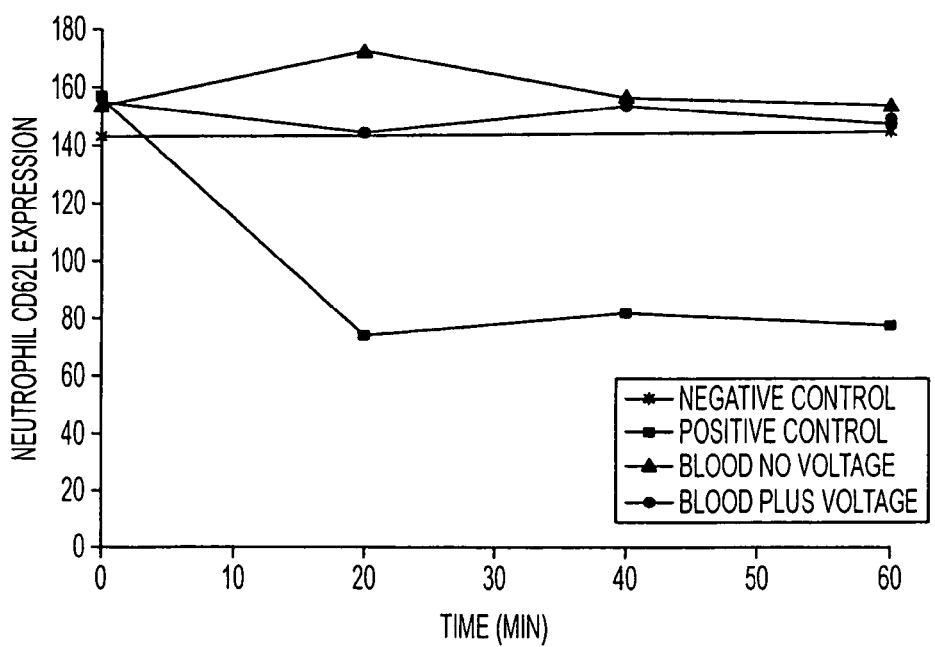
FIG. 18 shows effect of membrane based electrophoresis treatment on neutrophil activation in whole blood.

Whole blood was processed in The electrophoresis system with and without the application of an electrical potential. The application of an electric potential to whole blood did not cause significant neutrophil activation (FIG. 18).

Conclusion

The results of these experiments indicate that treatment of blood and plasma using The electrophoresis system technology with polyacrylamide membranes and an applied electrical potential was a biocompatible process. The results presented show that complement and coagulation systems, as well as cellular blood components, were not deleteriously affected by the electrophoresis system. Combining this biocompatibility data with previous findings that the electrophoresis system was capable of removing nitrogenous wastes indicates that this technology has significant potential in the treatment of renally compromised patients. The potential also existed for its use in therapeutic treatment of other disease states which require the removal of toxic material from body fluids.

Design of the Electrophoresis System

In this section, two electrophoresis devices were used; BF200 and DF100. The BF200 was an early model predominantly used for protein purifications/separations. The DF100 was designed for use as a small scale clinical dialysis device according to the present claims. Both of these embodiments fall within the scope of the present claims.

Three main issues were identified when using the BF200 unit. These were; high levels of hemolysis, temperature control of the blood and sanitization. The presence of zones of reduced fluid flow (dead zones), sharp surfaces and the use of an ice bucket to control temperature in the BF200 blood path were considered to contribute to the observed hemolysis. Temperature was also potentially problematic, as after blood passed through the separation unit the temperature rose above acceptable physiological limits. To overcome these problems, several modifications were made to produce the DF100 and these are described below.

Separation Unit and Housing

The separation unit and housing used to produce the DF100 was designed to be easily disassembled and sanitized by a variety of means, including autoclaving and chemical methods. The housing unit was able to enclose open vessels in S1, S2 and the buffer tank and prevent any cross-contamination between these areas. The separation unit was designed to be easily disassembled for cleaning purposes and also included an area for cartridge leakage decontamination. The DF100 also had far fewer dead zones or sharp internal surfaces than found in a BF200. All components for the DF100 could be sanitized by heat or chemical methods.

Temperature Control

Figure 19:
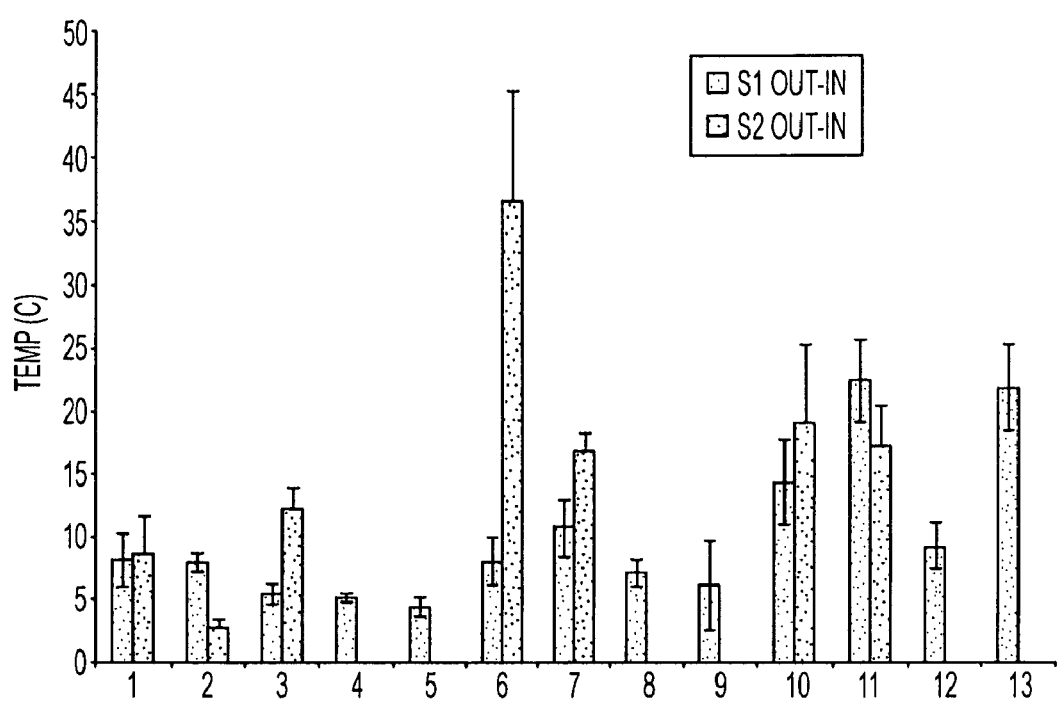
FIG. 19 shows temperature variations in S1 and S2 in variously configured membrane-based electrophoresis system. Numbering of each bar graph is set out below: Graph 1: normal flow, ice cooled dialysate, 2 streams, RS power supply; Graph 2: U/S counter current flow, ice cooled dialysate, 2 streams, RS power supply; Graph 3: normal flow, room temperature, 2 streams, RS power supply; Graph 4: normal flow, room temperature, 1 stream (S1), RS power supply; Graph 5: counter current flow, room temperature, 1 stream (S1), RS power supply; Graph 6: blood, normal flow, room temperature, 2 streams, RS power supply; Graph 7: blood, S1 counter current flow, room temperature, 2 streams, RS power supply; Graph 8: blood, normal flow, room temperature, 1 stream (S1), RS power supply; Graph 9: blood, counter current flow, room temperature, 1 stream (S1), RS power supply; Graph 10: blood, normal flow, room temperature, 2 stream, single pass, RS power supply; Graph 11: blood, counter current flow, room temperature, 2 stream, single pass, RS power supply; Graph 12: blood, normal flow, room temperature, 1 stream (S1), single pass, RS power supply; Graph 13: blood, counter current flow, room temperature, 1 stream (S1), single pass, RS power supply.

Temperature measurements during blood and plasma experiments in the BF200 suggested that the ice bucket method of controlling temperature was not ideal when working with blood/plasma. Analysis of different configurations (blood/plasma, parallel/counter current flow, plus/minus cooling, different power packs, single/multiple passes) of the BF200 demonstrated that, depending on the configuration, temperature could change between 5° C.–22° C. (FIG. 19). The results from the BF200 study did show that an average 8° C. increase occurred through the separation unit. An increase of 8° C. from a physiological 37° C. blood sample was considered to be unacceptable. To alleviate the temperature problem, the DF100 was configured to cool blood/plasma before entering the separation unit, the reverse of the BF200 and current dialysis therapies. Once blood had left the DF100 separation unit it was anticipated that the blood would be at a physiological temperature and be suitable for return to a patient. The DF100 fluid circuit design resulted in blood and buffer being cooled by an external heat exchanger/chiller unit before entering the separation unit. A heat exchange/chiller was used in place of the ice bucket to provide better temperature control of the system.

Temperature analysis of the DF100 fluid circuit showed that for the blood/plasma circuit a total temperature change of −0.8° C.±0.9° C. (average±S.D.) was obtained over a period of one hour. The DF100 showed a dramatic improvement from an increase of 8° C. observed when using a BF200.

The development of the DF100 was to improve hemolysis, blood temperature control and sanitization was followed by testing to determine whether the modifications altered the biocompatibility of the electrophoresis system.

Biocompatibility

Methods

To evaluate the biocompatibility whole blood and plasma were treated by the electrophoresis system and hemolysis, coagulation, complement and cellular activation were measured as per the Biocompatibility Aspects study.

Results

Hemolysis

Figure 20:
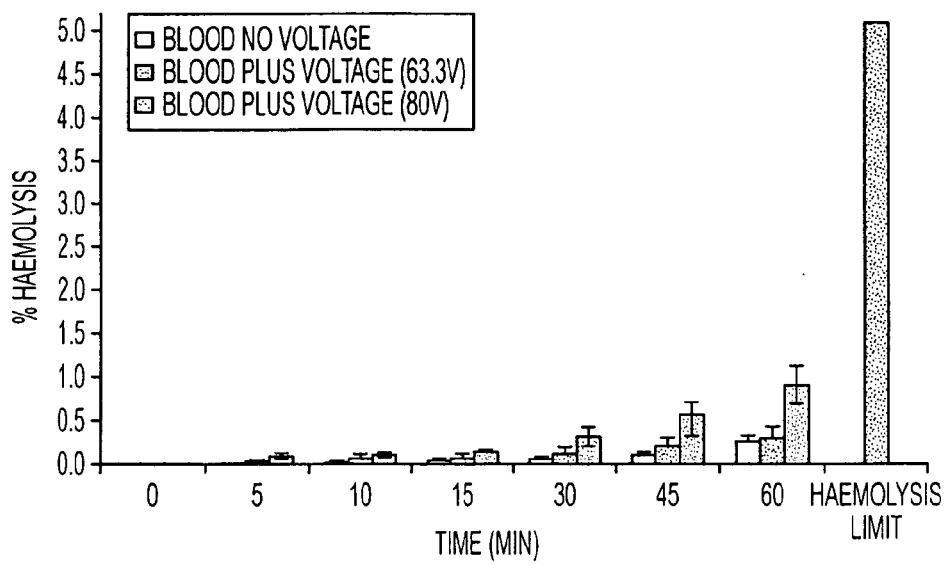
FIG. 20 shows effect of treatment using an electrophoresis system according to the present claims on hemolysis.

The percentage hemolysis was measured to determine the effect of an electrical potential on red blood cell lysis in anticoagulated whole blood. According to international standards, less than 5% hemolysis is acceptable for a medical device. The data demonstrated that with and without the application of an electrical potential, the observed hemolysis was within the acceptable range. The results also indicated that an electrical potential increases hemolysis on recirculating blood. The increased hemolysis was observed when an 80V electrical potential was applied to re-circulating blood. The application of 80V resulted in the lysis of less than 1% of red blood cells, which is less than the accepted international standards (5%) and is putatively caused by increase in temperature. However, after blood was recirculated with a 63.3V electrical potential, less than 0.5% hemolysis was observed. The hemolysis using 63.3V was within the error range of the 0V background values (FIG. 20).

Coagulation

Measurements of APTT time for the DF100 showed no difference to those observed in the BF200 biocompatibility investigation.

TAT Formation

Figure 21:
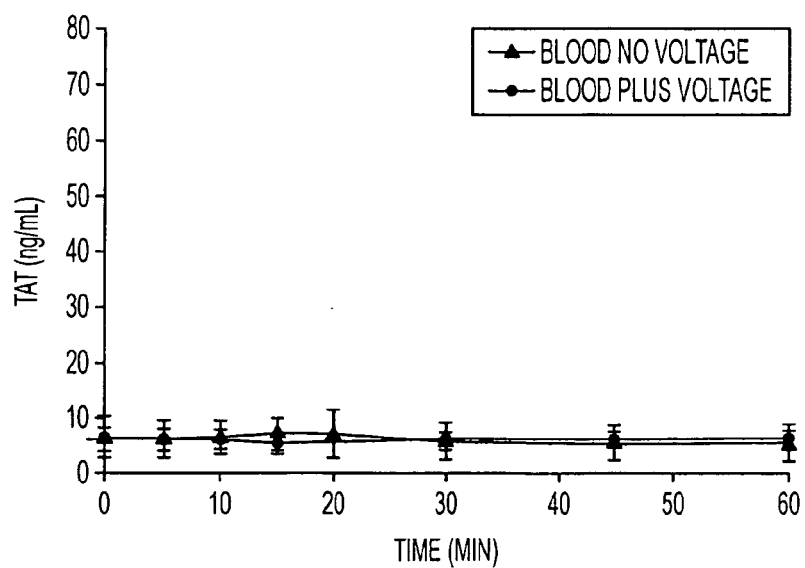
FIG. 21 shows effect of treatment using an electrophoresis system according to the present claims on coagulation, thrombin/antithrombin III complex (TAT) formation.

TAT formation in heparinised blood, indicated that coagulation activation did not occur. Testing of polyacrylonitrile, acrylonitrile copolymer (AN69), cuprophan and polysulphone generated between 75–175 ng/ml TAT after 27 minutes, while polyacrylamide membranes with an applied electrical potential maintained a TAT concentration of 6±2 ng/ml TAT within the 60 minute experiment (FIG. 21).

Complement C3a

Figure 22:
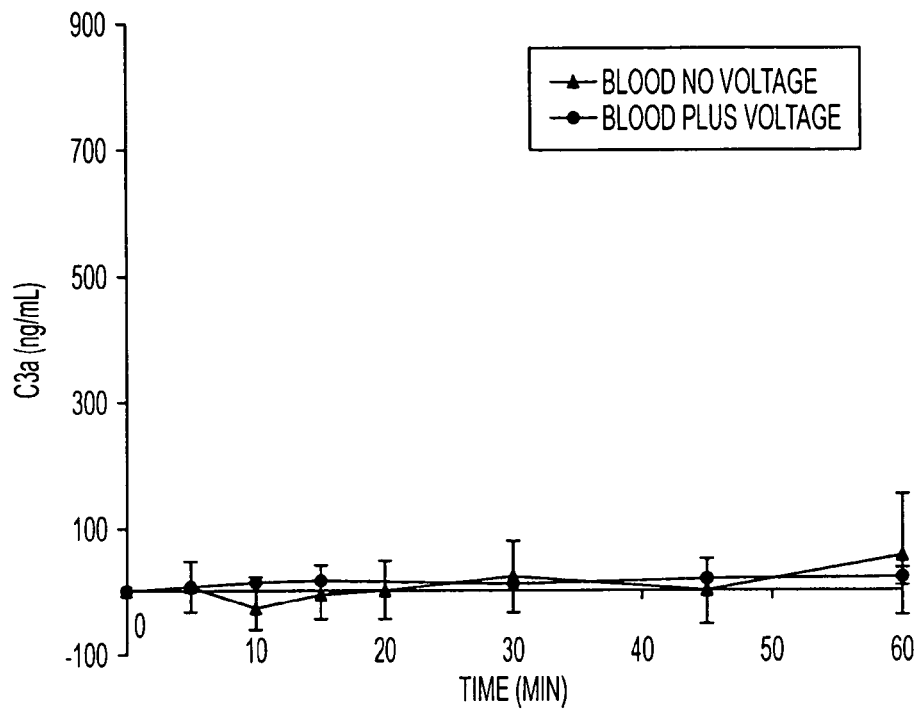
FIG. 22 shows effect of treatment using an electrophoresis system according to the present claims on complement (C3a) activation.

Measurements of C3a-desArg from heparinised blood indicated that polyacrylamide membranes and an electrical potential did not activate the complement pathway. In comparison testing of polyacrylonitrile, acrylonitrile copolymer (AN69), cuprophan and polysulphone between 80 ng/ml to in excess of 3000 ng/ml C3a were generated within 27 minutes from the baseline controls. With The electrophoresis system the largest increase in C3a levels was an average of 46 ng/ml from baseline controls, with no significant change in C3a activation with the application of an electrical potential (FIG. 22).

Conclusion

The data from the DF100 biocompatibility experiments showed an improvement in hemolysis. The coagulation and complement measurements suggested that a refinement to the process had been made, but there was not a significant improvement in these factors. Based on the comparison between 60V and 80V hemolysis data, a greater electrical potential could be used to speed the uremic reduction procedure, as hemolysis at 80V was less than 5%.

Electrical Potential

These experiments investigated the electrical potential that could be applied across blood in the DF100 using hemolysis as a measure of cellular damage.

Method

Blood (100 ml) was passed through the DF100 for one hour using a consort power supply limited to 2A and 150 W. The voltages applied were 63V, 80V, 100V, 125V, 150V and 200V. The hemolysis was measured at 0, 5, 10, 15, 30, 45 and 60 minutes, using the spectrophotometric method described previously in this document.

Results

Figure 23:
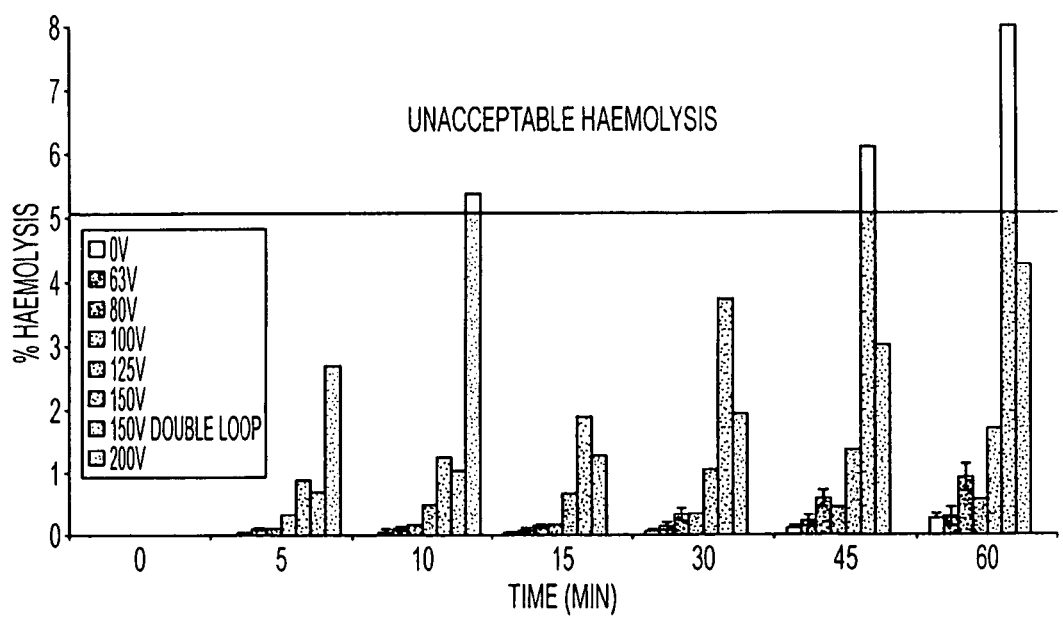
FIG. 23 shows effects of different voltage on hemolysis levels.

The results obtained from these experiments are primarily preliminary as data for 100V, 125V, 150V and 200V where n=1, however 0V, 63V and 80V where n≧4. The data demonstrated a trend in which lysis increase in a tentative "S" curve manner as voltage and wattage increases (FIG. 23). The increase in hemolysis appeared to be more attributed to the heat (wattage) generated in the separation unit rather than the actual electrical potential. As the wattage increased and the temperature of blood passing through the separation unit increased, a corresponding increase in lysis was observed. The benefit of cooling the blood more efficiently, was seen when the two 150V experiments were compared (FIG. 23). The blood path for one run was looped twice through the heat exchanger, while the other run had blood pass through the heat exchanger once. Passing the blood through the heat exchanger twice caused it to be cooled further before entering the separation unit, resulting in a decrease in hemolysis. However, there may be a limit to how low the blood can be cooled before entering the separation unit. The reason behind the blood cooling limit is that as temperature of blood/plasma decreases, proteins can potentially start to precipitate or biological systems can become activated on reheating to physiological conditions.

Phase 1 Animal Trials—Investigations into the Biocompatibility of the Electrophoresis System This study established an in vivo ovine model to determine the biocompatibility of the electrophoresis system technology. Six sheep were treated using the electrophoresis system and the effects on cells and plasma were analyzed. Six additional sheep were used to determine the baseline effects of the extracorporeal circuit without the electrophoresis system component. Biocompatibility was assessed in the treatment of both whole blood and plasma using an extracorporeal circuit and access via a carotid-jugular shunt. Biocompatibility was assessed by measuring the effect of experimental and control procedures on haematological and biochemical parameters.

Experimental Procedures

Figure 24:
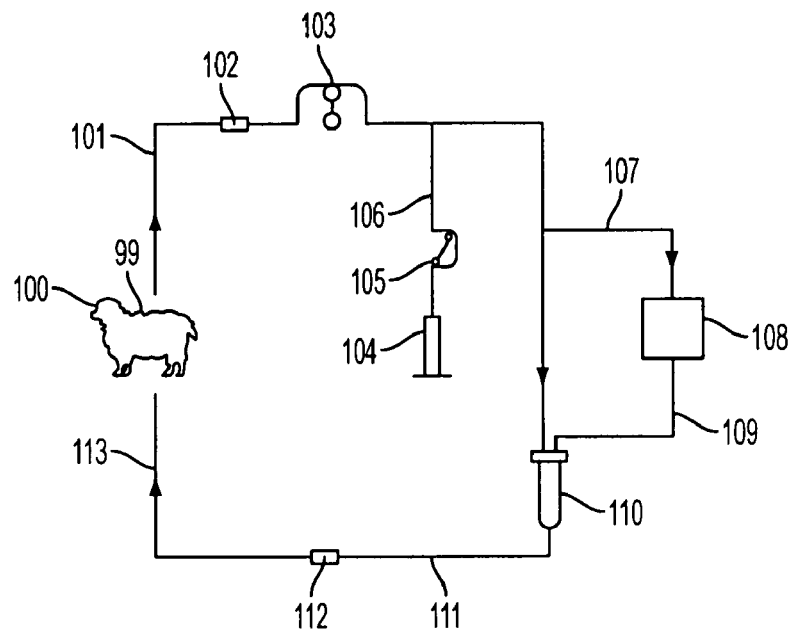
FIG. 24 shows blood circuit in an experimental sheep model.
Figure 25:
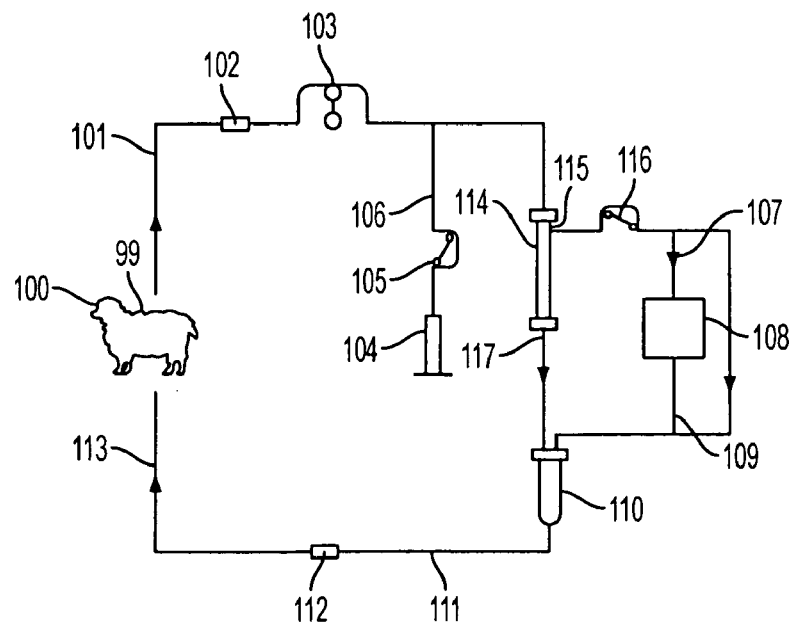
FIG. 25 shows plasma circuit in an experimental sheep model.

Sheep were used as the model to investigate the biocompatibility of the electrophoresis system when treating blood (FIG. 24) and plasma (FIG. 25). The sheep 99 used were healthy cross bred wethers, approximately 50 to 70 kg in weight and 2 years in age. In all procedures, vascular access was gained via direct cutdown to the animal's carotid artery and external jugular vein under general anaesthetic. A shunt 100 was inserted between carotid artery and jugular vein according to procedures outlined in An Ovine Carotid Jugular Shunt Model for Haemocompatibility Testing of Biomaterials (Tatarinoff V, Poole-Warren L A, Tunstell A and Schindhelm K. The Cooperative Research Centre for Cardiac Technology: Graduate School of Biomedical Engineering, University of New South Wales, Sydney 2052. An Ovine Carotid Jugular Shunt Model for Haemocompatibility Testing of Biomaterials).

The extracorporeal circuit was primed with normal saline with 10000 IU heparin added to the last bag. When used, the electrophoresis system cartridge was primed directly to drain. Anticoagulation was achieved by an initial bolus of heparin (5000 IU) followed by 5000 IU boluses of heparin hourly during the procedure. In some procedures using the electrophoresis system, the anticoagulation regime was supplemented with continuous infusion of heparin into the electrophoresis system line. The heparin infusion was achieved by using a pump 105 to transport the heparin solution 104 through a commercial sterile heparin line 106 into the arteriovenous circuit 101.

After blood access was achieved, a baseline blood sample was collected from the shunt. The arterial 101 and venous 113 lines were then connected to the carotid artery and jugular vein respectively and blood flow established through the blood circuit, using a Gambro blood pump 103. Blood was allowed to circulate for 10 minutes before arterial 102 and venous 112 blood samples were collected. In procedures where a plasma separator 114 was used, plasma flow was then established for a further five minutes before another set of arterial 102 and venous 112 blood samples was collected.

The electrophoresis system 108 process consisted of the cartridge together with a heat exchanger in line before the cartridge and the ancillary equipment required to maintain the temperature of the blood or plasma, along with a pump to transport the blood to the electrophoresis system 108. The electrophoresis system procedure was performed with and without electrical activation on whole blood (FIG. 24) or plasma (FIG. 25) separated from cellular components and reconstituted following processing. When whole blood was treated, blood was taken directly from the arteriovenous circuit 101 through tube 107 using the pump associated with the electrophoresis system 108. The blood was then treated by the electrophoresis system 108 and re-integrated, through tube 109, in a blood collection vessel 110. The blood was then returned to the sheep 99 through tube 111, sample port 112 and tubing 113. When plasma was treated, a membrane plasma separator 114 was used, in which plasma exited from the plasma outlet 115, while the cellular material of blood exited from the blood outlet 117. Plasma was transported from the plasma separator 114, with pump 116 from the plasma outlet port 115 and reconstituted with the cellular material through tube 117, into a blood collection vessel 110. The integrated whole blood in blood vessel 110 was transported back to the sheep 99, through tube 111, sample port 112 and tube 113. When plasma was treated by the electrophoresis system 108, plasma was taken directly from the plasma separator 114 using the pump associated with the electrophoresis system 108. The plasma was then treated by the electrophoresis system 108 and transported through tubing 109 and re-integrated with the cellular components of blood in the blood collection vessel 110. The blood was then returned to the sheep 99 via tubing 111, sample port 112 and tubing 113.

When electrical activation was used, it was performed in an ABAB format. Electrical activation was initially turned off for one hour (A), then turned on for one hour (B), off for one hour (A) and on again for one hour (B) to ascertain the effects of the electrical field on sheep blood chemistry.

Twelve sheep were used in the study. Whole blood was treated in three sheep with and without electrical activation (Group 1). Plasma was treated in a further three sheep with and without electrical activation (Group 2). For both Group 1 and Group 2 blood and plasma were processed through the electrophoresis system at 20 ml/min. Blood and plasma samples were taken from the arterial and venous sampling ports simultaneously after 5, 10, 30 and 60 minutes from time zero during each period of the electrophoresis system ABAB procedure (Table 1, Table 2). For both Group 1 and Group 2, after the final blood sample was collected, the sheep was euthanased and the contents of the bladder sampled. Six additional sheep were used for baseline studies to ascertain the effect of the surgery and extracorporeal blood circuit during the procedure. These procedures were conducted without the electrophoresis system in the circuit. Three sheep had procedures with whole blood and no plasma separation (Group 3) and three had procedures with plasma separation (Group 4). For Group 3 and 4, time zero was marked after the blood or plasma circuit was established. At t=5, 10, 30, 60, 90, 120, 180 and 240 minutes from time zero, arterial and venous blood samples were collected (Table 3, Table 4). After the final blood sample was taken, the sheep was euthanased and the contents of the bladder sampled.

Pulse, respiration rate, oxygen partial pressure ($SpO_2$) and temperature were recorded at 10 minute intervals during all procedures. Blood and urine samples taken before, during and after the procedure were tested to determine any effects of the procedure on the cellular components of the blood as well as liver function and electrolytes. Blood samples were tested by an external laboratory for the analytes set out in Table 5:

TABLE 1

Procedure chart group 1 - whole blood with the electrophoresis system

| Time | Sample | Defined time/procedure | Sample |
|---|---|---|---|
| | −1 | Before connection to circuit<br>HEPARIN BOLUS | baseline blood sample from shunt |
| | −2 | After connection to circuit for 10 mins min | baseline blood circuit blood<br>sample from arterial bloodline port |
| | | Unclamp circuit t = 0 | |

TABLE 1-continued

Procedure chart group 1 - whole blood with the electrophoresis system

| Time | Sample | Defined time/procedure | Sample |
|---|---|---|---|
| | −3 | t = 5 | arterial and |
| | −4 | | post electrophoresis blood samples |
| | −5 | t = 10 | arterial and |
| | −6 | | post electrophoresis blood samples |
| | −7 | t = 30 | arterial and |
| | −8 | HEPARIN BOLUS | post electrophoresis blood samples |
| | −9 | t = 60 | arterial and |
| | −10 | | post electrophoresis blood samples |
| | | Turn electrophoresis system on | |
| | −11 | t = + 5 | arterial and |
| | −12 | | post electrophoresis blood samples |
| | −13 | t = + 10 | arterial and |
| | −14 | | post Electrophoresis blood samples |
| | −15 | t = + 30 | arterial and |
| | −16 | HEPARIN BOLUS | post Electrophoresis blood samples |
| | −17 | t = + 60 | arterial and |
| | −18 | | post Electrophoresis blood samples |
| | | Turn Electrophoresis system off | |
| | −19 | t = + 5 | arterial and |
| | −20 | | post Electrophoresis blood samples |
| | −21 | t = + 10 | arterial and |
| | −22 | | post Electrophoresis blood samples |
| | −23 | t = + 30 | arterial and |
| | −24 | HEPARIN BOLUS | post Electrophoresis blood samples |
| | −25 | t = + 60 | arterial and |
| | −26 | | post Electrophoresis blood samples |
| | | Turn Electrophoresis system off | |
| | −27 | t = + 5 | arterial and |
| | −28 | | post Electrophoresis blood samples |
| | −29 | t = + 10 | arterial and |
| | −30 | | post Electrophoresis blood samples |
| | −31 | t = + 30 | arterial and |
| | −32 | HEPARIN BOLUS | post Electrophoresis blood samples |
| | −33 | t = + 60 | arterial and |
| | −34 | | post Electrophoresis blood samples |
| | | Turn Electrophoresis system off ethanase sheep | |
| | −35 | Sample bladder | urine sample |

TABLE 2

Procedure chart group 2 - plasma with electrophoresis system

| Time | Sample | Defined time/procedure | Sample |
|---|---|---|---|
| | −1 | Before connection to circuit | baseline blood sample from shunt HEPARIN BOLUS |
| | −2 | After connection to circuit | baseline blood circuit blood |
| | −3 | for 10 mins min | sample from arterial and venous bloodline ports |

TABLE 2-continued

Procedure chart group 2 - plasma with electrophoresis system

| Time | Sample | Defined time/procedure | Sample |
|---|---|---|---|
| | −4 | Unclamp plasma circuit and allow to run for 5 mins min | baseline plasma circuit blood sample from arterial and venous bloodline ports |
| | −5 | | |
| | | Unclamp circuit t = 0 | |
| | −6 | t = 5 | arterial and |
| | −7 | | post Electrophoresis blood samples |
| | −8 | t = 10 | arterial and |
| | −9 | | post Electrophoresis blood samples |
| | −10 | t = 30 | arterial and |
| | −11 | HEPARIN BOLUS | post Electrophoresis blood samples |
| | −12 | t = 60 | arterial and |
| | −13 | | post Electrophoresis blood samples |
| | | Turn Electrophoresis system on | |
| | −14 | t = + 5 | arterial and |
| | −15 | | post Electrophoresis blood samples |
| | −16 | t = + 10 | arterial and |
| | −17 | | post Electrophoresis blood samples |
| | −18 | t = + 30 | arterial and |
| | −19 | HEPARIN BOLUS | post Electrophoresis blood samples |
| | −20 | t = + 60 | arterial and |
| | −21 | | post Electrophoresis blood samples |
| | | Turn Electrophoresis system off | |
| | −22 | t = + 5 | arterial and |
| | −23 | | post Electrophoresis blood samples |
| | −24 | t = + 10 | arterial and |
| | −25 | | post Electrophoresis blood samples |
| | −26 | t = + 30 | arterial and |
| | −27 | HEPARIN BOLUS | post Electrophoresis blood samples |
| | −28 | t = + 60 | arterial and |
| | −29 | | post Electrophoresis blood samples |
| | | Turn Electrophoresis system on | |
| | −30 | t = + 5 | arterial and |
| | −31 | | post Electrophoresis blood samples |
| | −32 | t = + 10 | arterial and |
| | −33 | | post Electrophoresis blood samples |
| | −34 | t = + 30 | arterial and |
| | −35 | HEPARTN BOLUS | post Electrophoresis blood samples |
| | −36 | t = + 60 | arterial and |
| | −37 | | post Electrophoresis blood samples |
| | | Turn Electrophoresis system off Euthanase sheep | |
| | −38 | Sample bladder | urine sample |

TABLE 3

Procedure chart group 3 - whole blood without electrophoresis system

| Time | Sample | Defined time / procedure | Sample |
|---|---|---|---|
| | −1 | Before connection to circuit<br>HEPARIN BOLUS | baseline blood sample from shunt |
| | −2 | After connection to circuit for 10 mins min t = 0 | baseline blood circuit blood sample from arterial bloodline port |
| | −3 | t = 5 | arterial blood sample |
| | −4 | t = 10 | arterial blood sample |
| | −5 | t = 30<br>HEPARIN BOLUS | arterial blood sample |
| | −6 | t = 60 | arterial blood sample |
| | −7 | t = 90<br>HEPARIN BOLUS | arterial blood sample |
| | −8 | t = 120<br>t = 150<br>HEPARIN BOLUS | arterial blood sample |
| | −9 | t = 180<br>t = 210<br>HEPARIN BOLUS | arterial blood sample |
| | −10 | t = 240<br>Euthanase sheep | arterial blood sample |
| | −11 | Sample bladder | urine sample |

TABLE 4

Procedure chart group 4 - plasma without electrophoresis system

| Time | Sample | Defined time/procedure | Sample |
|---|---|---|---|
| | −1 | Before connection to circuit<br>HEPARIN BOLUS | baseline blood sample from shunt |
| | −2<br>−3 | After connection to circuit for 10 mins min | baseline blood circuit blood sample from arterial and venous bloodline ports |
| | −4<br>−5 | Unclamp plasma circuit and allow to run for 5 mins min | baseline plasma circuit blood sample from arterial and venous bloodline ports |
| | −6<br>−7 | t = 5 | arterial and<br>venous blood samples |
| | −8<br>−9 | t = 10 | arterial and<br>venous blood samples |
| | −10<br>−11 | t = 30<br>HEPARIN BOLUS | arterial and<br>venous blood samples |
| | −12<br>−13 | t = 60 | arterial and<br>venous blood samples |
| | −14<br>−15 | t = 90<br>HEPARIN BOLUS | arterial and<br>venous blood samples |
| | −16<br>−17 | t = 120 | arterial and<br>venous blood samples |
| | −18<br>−19 | t = 150<br>HEPARIN BOLUS<br>t = 180 | arterial and<br>venous blood samples |
| | −20<br>−21 | t = 210<br>HEPARIN BOLUS<br>t = 240<br>Euthanase sheep | arterial and<br>venous blood samples |
| | −22 | Sample bladder | urine sample |

TABLE 5

Blood analytes tested externally

| BIOCHEMISTRY | HEMATOLOGY |
|---|---|
| Glucose | RBC |
| Urea | Hb |
| Creatinine | PCV |
| Protein | MCV |

TABLE 5-continued

Blood analytes tested externally

| BIOCHEMISTRY | HEMATOLOGY |
| --- | --- |
| Albumin | MCH |
| Globulin | MCHC |
| A-G ratio | WCC |
| T-bilirubin | Differential |
| C-bilirubin | bands |
| GLDH | neutrophils |
| Alkaline phosphatase | lymphocytes |
| AST | monocytes |
| Gamma GT | eosinophils |
| B-OH BUT | basophils |
| CK | others |
| Magnesium | Platelets |
| Calcium | Gross hemolysis |
| Phosphate | RDW |
| Sodium | |
| Potassium | |
| Chloride | |
| Bicarbonate | |

Statistical Methods

A weighted mean, equivalent to an "area under the curve", was calculated for each one-hour period. This was calculated using the trapezoidal method. Note that when the average is calculated this way, the observations at 30 and 60 minutes carry much more weight than the observations at 0, 5 and 10 minutes. Note also that the pre-procedure (baseline) sample was not included in the calculation.

The factors that might affect the measured variables are the experimental group, G={BG, PG, B, P}, the time period P={A1, B1, A2, B2}, the sampling site SI={A,V}, and the sheep S={1,2, . . . ,12}. The experimental group can be treated as one factor with 4 levels or as two crossed factors, plasma PL={0,1 } and the electrophoresis system GR= {0,1 }.

The sheep factor is a catch-all that includes the random variation due the particular sheep selected for the procedure as well as all other day-to-day variation that cannot otherwise be accounted for. The concentration of a solute during the procedure may reflect the baseline, pre-procedure level. The analysis can take this into account.

The experiment design was of a 'repeated measures type' with two between-sheep factors, PL and GR, and two within-sheep factors, P and SI. Tests of the between-sheep factors, PL and GR, were performed using analysis of co-variance on the means, calculated over the eight observations (4 periods×2 sites) for each sheep, with the baseline level (the initial arterial sample) as the covariate. This method is recommended by Frison and Pocock (Frison L and Pocock S J: Repeated measures in clinical trials: Analysis using mean summary statistics and its implications for design. Statistics in Medicine 11:1685–1704 (1992)) as the optimum way to adjust for the effect of variation in baseline levels. For example, this method determines if the average level X in the experiments with the electrophoresis system in the circuit different from the average level in experiments without the electrophoresis system.

Overall tests of the within-sheep factors, P and SI, and their interactions with PL and GR were performed using repeated-measures analysis of variance with the Huynh-Feldt correction factor (StataCorp. 1999. Stata Statistical Software: Release 6.0. College Station Tex: Stata Corporation). These tests determine if the levels of Y changed during the procedure and whether the pattern of differences was affected by the electrophoresis system.

Tests of specific contrasts were performed as described by Harris (Harris R J. "Anova: An Analysis of Variance Primer", F. E. Peacock, Itasca Ill., 1994). These tests explore the pattern of differences, and demonstrate if the pattern was different when the electrophoresis system was in the circuit or when the power was on.

A number of contrasts among the levels of P and SI were calculated for each sheep and each contrast was tested as the dependent variable in an ordinary univariate analysis of variance against PL and GR, including an additional test that the overall mean of the variable is different from zero. For example, in the anova of a contrast P1 against PL and GR, the F-ratio for GR would be a test of the P1×GR interaction.

Four contrasts among the time periods were tested. The coefficients are listed below along with the contrast S1 comparing arterial and venous. P1 is a contrast between B and A periods (corresponding to power on and power off when the electrophoresis system was used). P2 compares the second AB cycle with the first and P3 compares the B–A difference in the second cycle with the B–A difference in the first cycle. These three contrasts are orthogonal (the dot products of their coefficient vectors is zero) and together they account for all variation among the 4 time periods. Contrast P4 simply compares B and A during the first cycle.

If there is a steady increasing or decreasing trend in the level of solute Y, the value of P2 will be twice the value of P1 and P3 will be zero. If the electrophoresis system power on causes the level of Y to rise, there will be a positive P1 in the electrophoresis system groups only; thus the GR×P1 interaction would be positive.

Specific Tests That Were of Primary and a Priori Interest

The P*GR interaction. Was the pattern over time, if any, different when the electrophoresis system was in the circuit? This was tested in the repeated measures anova.

P1*GR interaction. Was the B–A difference dependent on the electrophoresis system? This was tested by performing anova on contrast P1.

P4*GR. Was the B1–A1 difference dependent on the electrophoresis system? The power was actually not on as much in the second cycle because of clotting, so this comparison might be more revealing of any effect of ehe electrophoresis system activation.

Results & Discussion

This study assessed the biocompatibility of the electrophoresis system. The electrophoresis system poses several issues relating to biocompatibility. Firstly, the design and materials of the cartridge, the membranes, the heat exchanger and the tubing may all affect the biocompatibility of the procedure. Secondly, the effect of the electrical field on the blood or plasma was established in an ex vivo setting.

During the trial, all animals survived the extracorporeal procedures and in general, the electrophoresis system procedures were well tolerated by the animals. During the study more than 16000 data points were collected and analyzed. There were no statistically significant adverse effects seen between the control and treatment groups for any biochemical or haematological value.

The results of between-sheep tests by analysis of covariance are summarized in Table 6—Ancova Summary. The results of the overall within-sheep tests for the effects of sampling site and time period by repeated measures analysis of variance are summarized in Table 7—Repeated Measures Summaries—SI and P. The summary of the statistical analysis of specific within-sheep contrasts in as Table 8—Within Sheep Contrasts.

The statistical analysis of the biochemical and haematological data indicated that globulin, albumin and total protein levels were affected by the presence of the electrophoresis system in the circuit. The effect could be broken down into two components: an initial drop due to the greater haemodilution when the electrophoresis system was in the circuit and a decreasing trend due the greater sampling during the electrophoresis system procedures. It is also possible that proteins smaller than the membranes were removed by the electrophoresis system particularly when the electrical field was activated.

Globulin, albumin and total protein levels decreased initially in all animals due to the haemodilution effect of the extracorporeal circuit and thereafter remained stable or continued to decrease slowly during the procedures. Analysis of covariance indicated that the plasma filter and the electrophoresis system both reduced mean protein levels and that their effects were additive. This would be expected as each component added to the extracorporeal volume. There were also significant differences in levels between time periods and a significant P*GR interaction. The within-sheep contrasts P1 and P2 were highly significant for globulin, albumin and total protein and the P2*GR interaction was significant for all three ($p<0.05$). This effect resulted from the increased blood sampling that occurred during the electrophoresis system procedures. The effect was more pronounced for globulin and total protein than albumin due to the fact that the lower molecular weight albumin would be more rapidly replenished from extravascular stores during the procedures than the larger proteins. Thus the albumin:globulin ratio increased with time.

In almost all animals, glucose levels remained stable or increased slightly during the four hour procedure. The results indicated a generally increasing trend in glucose levels in all groups unrelated to the presence of the electrophoresis system.

Total and conjugated bilirubin levels were relatively stable in most animals with a slow increase apparent in both over the course of the procedure. However, it is seems safe to conclude that these trends were unrelated to the presence of the electrophoresis system in the procedure.

GLDH levels were stable in the control and treatment animals whereas alkaline phosphatase levels tended to increase over the course of the procedures. The statistical analysis indicated no significant effect of plasma filtration or the electrophoresis system on GLDH or alkaline phosphatase levels AST and GammaGT levels were relatively stable for all animals throughout the procedures with a slow decline in AST seen over the course of the procedures in most animals. The statistical analysis suggested that there was a significant difference between arterial and venous levels of Gamma GT unrelated to the presence of the electrophoresis system.

B-OHBUT and CK levels were relatively stable for all animals throughout the procedures with a slow increase seen over the course of the procedures in most animals. One electrophoresis system treated blood animal exhibited a sharp decrease in CK levels when the electrical field was deactivated for the first time. The level in this animal then remained low for the remainder of the procedure. Venous levels of CK were consistently higher than arterial by an average of 2.5 U/l across all groups and periods.

Biochemical values such as urea, creatinine and most electrolytes were relatively stable during the extracorporeal procedures as expected.

Potassium levels were relatively stable in all animals and the statistical analysis suggests an increasing trend in all groups unrelated to the presence of the electrophoresis system in the procedure.

Bicarbonate levels showed small increases in nearly all animals with the pattern consistent across the four groups. Venous levels were consistently lower than arterial by an average of 0.6 mM across all groups and periods.

The statistical analysis suggests that magnesium and calcium levels decreased during the procedures unrelated to the presence of the electrophoresis system in the circuit.

RBC, PCV and hemoglobin levels decreased initially due to the haemodilution effect of the extracorporeal circuit then, in most animals, remained relatively stable or showed a slow decrease due to sample collection for the remainder of the procedure. The statistical analysis suggested that differences between groups were not significant for RBC, PCV or hemoglobin. There were no other significant effects.

MCV, MCH and MCHC were relatively stable in most animals throughout the procedures. The statistical analysis suggested that differences between groups were not significant for MCV, MCH or MCHC.

White cell numbers (WCC) fell in all cases at the start of the procedure. The effect was most dramatic in the plasma groups and was substantially if not entirely due to a fall in neutrophil numbers. In the plasma groups, neutrophils were effectively absent from the circulation for the first 30–60 minutes. Thereafter, cell counts increased steadily throughout the procedure in all groups. As a consequence of this early neutropenia, mean WCC were significantly lower in the plasma groups ($p=0.02$). Mean neutrophil numbers were also lower but the difference did not meet statistical significance ($p=0.06$). According to the repeated measures analysis of variance, the increasing trend in cell counts was highly significant for both WCC and neutrophils, and the trend was not influenced by the plasma filter or the electrophoresis system.

Lymphocyte, eosinophil and monocyte levels were relatively stable in most animals.

Bladder urine volumes were generally low following the procedures. The fluid balance of the animals was affected by several factors. Firstly, connection to the extracorporeal circuits resulted in a net loss of between 100 ml (blood control) and 250 ml (plasma) at the initiation of the procedure. This was balanced with an equivalent volume of heparinised saline from the circuit on connection. Secondly, the total volume of samples ranged from 150 ml (blood control) to 275 ml (plasma). Thirdly, fluid loss due to respiration could account for up to 300 ml in a 4 hour procedure. The latter fluid losses were replaced with Hartman's solution given intravenously during the procedure. However, on average, 3 litres of Hartman's was administered in each procedure resulting in probable fluid overload for some of the animals.

TABLE 6

Test of between-sheep factors: Ancova model

| variable | baseline coef | baseline F | baseline p | PL F | PL p | GR F | GR p | PL*GR F | PL*GR p |
|---|---|---|---|---|---|---|---|---|---|
| glucose | 0.79 | 1.05 | 0.339 | 0.77 | 0.410 | 0.03 | 0.863 | 0.81 | 0.397 |
| urea | 0.86 | 21.46 | 0.002 | 0.05 | 0.826 | 0.07 | 0.797 | 0.02 | 0.900 |
| creat | 1.38 | 18.08 | 0.004 | 0.32 | 0.591 | 0.08 | 0.790 | 0.64 | 0.449 |
| prot | 0.64 | 9.11 | 0.019 | 8.85 | 0.021 | 8.73 | 0.021 | 0.13 | 0.728 |
| albumin | 0.69 | 7.59 | 0.028 | 5.14 | 0.058 | 6.27 | 0.041 | 0.01 | 0.934 |
| globulin | 0.72 | 29.72 | 0.001 | 12.44 | 0.010 | 5.74 | 0.048 | 1.72 | 0.231 |
| agratio | 0.95 | 77.49 | 0.000 | 4.06 | 0.084 | 1.10 | 0.328 | 4.01 | 0.085 |
| tbili | 0.60 | 29.91 | 0.001 | 1.56 | 0.252 | 1.83 | 0.219 | 0.38 | 0.555 |
| cbili | 0.26 | 1.40 | 0.275 | 0.69 | 0.434 | 0.55 | 0.484 | 0.00 | 0.952 |
| gldh | 0.93 | 6287.21 | 0.000 | 2.16 | 0.185 | 2.52 | 0.157 | 0.59 | 0.467 |
| alkphos | 0.34 | 1.07 | 0.335 | 0.00 | 0.996 | 0.01 | 0.934 | 0.07 | 0.797 |
| ast | 0.86 | 646.21 | 0.000 | 5.20 | 0.057 | 2.98 | 0.128 | 0.78 | 0.408 |
| gammagt | 0.86 | 115.80 | 0.000 | 4.71 | 0.066 | 5.14 | 0.058 | 0.06 | 0.820 |
| bohbut | 0.26 | 2.09 | 0.191 | 1.17 | 0.315 | 0.80 | 0.402 | 0.68 | 0.437 |
| ck | 0.65 | 28.78 | 0.001 | 1.64 | 0.241 | 5.01 | 0.060 | 4.41 | 0.074 |
| mg | 0.12 | 0.17 | 0.695 | 1.10 | 0.329 | 0.66 | 0.445 | 0.00 | 0.946 |
| ca | 0.76 | 12.64 | 0.009 | 0.24 | 0.636 | 0.00 | 0.979 | 0.00 | 0.964 |
| phos | 1.03 | 11.80 | 0.011 | 2.19 | 0.182 | 0.29 | 0.608 | 0.02 | 0.885 |
| caprat | 0.64 | 14.76 | 0.006 | 0.72 | 0.425 | 0.63 | 0.454 | 0.71 | 0.427 |
| na | 0.72 | 9.38 | 0.018 | 0.00 | 0.954 | 0.01 | 0.911 | 2.08 | 0.193 |
| k | 0.94 | 9.81 | 0.017 | 0.73 | 0.420 | 0.02 | 0.893 | 7.22 | 0.031 |
| cl | 1.05 | 29.58 | 0.001 | 0.17 | 0.695 | 4.23 | 0.079 | 1.79 | 0.223 |
| bicarb | 0.57 | 4.87 | 0.063 | 0.79 | 0.405 | 0.25 | 0.631 | 0.01 | 0.914 |
| angap | 0.61 | 4.75 | 0.066 | 1.23 | 0.304 | 2.25 | 0.177 | 0.66 | 0.443 |
| nakrat | 0.92 | 10.39 | 0.015 | 0.60 | 0.464 | 0.01 | 0.914 | 7.18 | 0.032 |
| rbc | 1.04 | 22.41 | 0.002 | 1.03 | 0.344 | 0.21 | 0.662 | 2.18 | 0.183 |
| hb | 1.00 | 11.01 | 0.013 | 0.64 | 0.448 | 0.01 | 0.929 | 2.17 | 0.185 |
| pcv | 1.04 | 26.41 | 0.001 | 1.01 | 0.349 | 0.30 | 0.602 | 0.96 | 0.359 |
| mcv | 0.96 | 223.24 | 0.000 | 0.66 | 0.445 | 1.19 | 0.312 | 0.50 | 0.501 |
| mch | 0.79 | 94.26 | 0.000 | 0.13 | 0.730 | 0.00 | 0.982 | 1.94 | 0.207 |
| mchc | 0.30 | 2.86 | 0.134 | 0.05 | 0.833 | 3.60 | 0.100 | 0.37 | 0.560 |
| wcc | 0.35 | 1.65 | 0.239 | 8.82 | 0.021 | 0.19 | 0.678 | 0.06 | 0.813 |
| neut | 0.76 | 2.89 | 0.133 | 4.90 | 0.062 | 0.10 | 0.758 | 0.40 | 0.547 |
| lymph | 0.47 | 6.91 | 0.034 | 4.71 | 0.067 | 0.50 | 0.503 | 0.02 | 0.882 |
| mono | 0.16 | 2.15 | 0.186 | 2.05 | 0.195 | 0.25 | 0.635 | 0.23 | 0.649 |
| eosin | 0.39 | 55.76 | 0.000 | 0.00 | 0.959 | 0.26 | 0.628 | 2.05 | 0.195 |
| rdw | 0.49 | 8.21 | 0.024 | 0.01 | 0.906 | 0.09 | 0.771 | 2.93 | 0.131 |

TABLE 7

Repeated measures Anova - SI and P, Tests on SI:

| | SI F | SI p' | SI*PL F | SI*PL p' | SI*GR F | SI*GR p' | SI*PL*GR F | SI*PL*GR p' | |
|---|---|---|---|---|---|---|---|---|---|
| glucose | 2.86 | 0.129 | 2.32 | 0.166 | 1.65 | 0.236 | 1.84 | 0.212 | |
| urea | 0.01 | 0.913 | 1.64 | 0.236 | 1.21 | 0.304 | 0.00 | 0.990 | |
| creat | 0.05 | 0.834 | 0.09 | 0.775 | 0.65 | 0.443 | 0.24 | 0.636 | |
| prot | 1.65 | 0.235 | 1.86 | 0.209 | 0.00 | 0.953 | 0.57 | 0.472 | |
| albumin | 0.55 | 0.481 | 5.75 | 0.043 | 0.64 | 0.447 | 1.20 | 0.305 | * |
| globulin | 2.61 | 0.145 | 0.07 | 0.804 | 0.19 | 0.671 | 1.85 | 0.211 | |
| agratio | 0.83 | 0.388 | 1.35 | 0.278 | 0.06 | 0.818 | 1.86 | 0.210 | |
| tbili | 3.34 | 0.105 | 2.40 | 0.160 | 6.93 | 0.030 | 2.23 | 0.174 | * |
| cbili | 4.88 | 0.058 | 4.71 | 0.062 | 2.39 | 0.161 | 3.52 | 0.097 | |
| gldh | 0.03 | 0.874 | 0.94 | 0.362 | 0.06 | 0.806 | 0.19 | 0.675 | |
| alkphos | 14.89 | 0.005 | 3.39 | 0.103 | 2.57 | 0.147 | 0.63 | 0.451 | |
| ast | 8.64 | 0.019 | 1.44 | 0.265 | 0.17 | 0.694 | 6.24 | 0.037 | |
| gammagt | 21.16 | 0.002 | 0.15 | 0.709 | 0.55 | 0.478 | 0.10 | 0.763 | |
| bohbut | 3.36 | 0.104 | 0.37 | 0.558 | 0.01 | 0.925 | 0.13 | 0.733 | |
| ck | 11.08 | 0.010 | 0.42 | 0.534 | 0.39 | 0.549 | 0.95 | 0.357 | |
| mg | 8.97 | 0.017 | 0.73 | 0.418 | 2.50 | 0.153 | 0.16 | 0.696 | |
| ca | 1.04 | 0.338 | 3.25 | 0.109 | 3.64 | 0.093 | 0.12 | 0.743 | |
| phos | 3.52 | 0.098 | 6.54 | 0.034 | 8.18 | 0.021 | 1.81 | 0.215 | * |
| caprat | 1.43 | 0.266 | 0.77 | 0.406 | 1.07 | 0.331 | 1.07 | 0.331 | |
| na | 4.56 | 0.065 | 0.11 | 0.748 | 2.55 | 0.149 | 5.26 | 0.051 | |
| k | 3.47 | 0.100 | 0.73 | 0.418 | 0.86 | 0.382 | 1.25 | 0.296 | |
| cl | 1.12 | 0.321 | 1.19 | 0.306 | 0.23 | 0.642 | 3.40 | 0.102 | |
| bicarb | 21.38 | 0.002 | 0.04 | 0.848 | 0.29 | 0.607 | 0.44 | 0.527 | |

TABLE 7-continued

Repeated measures Anova - SI and P, Tests on SI:

| | SI F | SI p' | SI*PL F | SI*PL p' | SI*GR F | SI*GR p' | SI*PL*GR F | SI*PL*GR p' | |
|---|---|---|---|---|---|---|---|---|---|
| angap | 8.99 | 0.017 | 0.96 | 0.355 | 0.08 | 0.789 | 0.01 | 0.909 | |
| nakrat | 3.40 | 0.103 | 1.08 | 0.330 | 1.33 | 0.283 | 0.65 | 0.444 | |
| rbc | 2.77 | 0.135 | 2.66 | 0.141 | 0.00 | 0.966 | 0.10 | 0.755 | |
| hb | 0.85 | 0.385 | 1.66 | 0.234 | 0.04 | 0.839 | 0.00 | 0.969 | |
| pcv | 4.07 | 0.078 | 4.07 | 0.078 | 0.07 | 0.803 | 0.01 | 0.920 | |
| mcv | 0.84 | 0.387 | 7.88 | 0.023 | 0.27 | 0.616 | 2.66 | 0.141 | * |
| mch | 1.86 | 0.210 | 0.07 | 0.805 | 0.12 | 0.733 | 2.87 | 0.128 | |
| mchc | 2.47 | 0.154 | 0.83 | 0.388 | 0.91 | 0.368 | 0.57 | 0.471 | |
| wcc | 1.20 | 0.305 | 0.18 | 0.685 | 0.56 | 0.475 | 1.37 | 0.275 | |
| neut | 0.01 | 0.925 | 1.36 | 0.278 | 0.00 | 0.978 | 2.13 | 0.183 | |
| lymph | 0.11 | 0.744 | 1.88 | 0.207 | 0.05 | 0.821 | 0.22 | 0.653 | |
| mono | 0.00 | 0.970 | 0.40 | 0.542 | 0.61 | 0.458 | 0.45 | 0.522 | |
| eosin | 0.05 | 0.832 | 3.47 | 0.099 | 0.49 | 0.504 | 0.10 | 0.761 | |
| baso | 1.52 | 0.252 | 1.10 | 0.325 | 0.52 | 0.491 | 0.82 | 0.390 | |
| other | 0.99 | 0.349 | 0.99 | 0.349 | 1.01 | 0.345 | 1.01 | 0.345 | |
| rdw | 0.05 | 0.825 | 0.49 | 0.505 | 1.73 | 0.225 | 0.21 | 0.661 | |

TABLE 8

Repeated measures Anova - SI and P, Tests on P:

|  | HF | P | | P*PL | | P*GR | | P*PL*GR | | |
|---|---|---|---|---|---|---|---|---|---|---|
|  |  | F | p' | F | p' | F | p' | F | p' | |
| glucose | 0.51 | 15.56 | 0.001 | 2.12 | 0.167 | 0.08 | 0.878 | 2.10 | 0.169 | |
| urea | 0.58 | 1.28 | 0.304 | 0.51 | 0.590 | 2.03 | 0.172 | 0.85 | 0.434 | |
| creat | 0.53 | 3.03 | 0.092 | 3.65 | 0.064 | 0.15 | 0.814 | 0.42 | 0.623 | |
| prot | 1.00 | 23.14 | 0.000 | 0.96 | 0.427 | 4.83 | 0.009 | 0.00 | 1.000 | ** |
| albumin | 1.00 | 22.36 | 0.000 | 0.37 | 0.775 | 4.04 | 0.019 | 0.01 | 0.999 | * |
| globulin | 0.98 | 20.48 | 0.000 | 1.88 | 0.161 | 5.00 | 0.008 | 0.01 | 0.998 | ** |
| agratio | 1.00 | 5.91 | 0.004 | 2.49 | 0.084 | 1.28 | 0.302 | 0.11 | 0.956 | |
| tbili | 0.94 | 11.92 | 0.000 | 6.31 | 0.003 | 1.81 | 0.175 | 0.66 | 0.574 | ** |
| cbili | 1.00 | 5.61 | 0.005 | 2.98 | 0.051 | 0.21 | 0.887 | 0.63 | 0.601 | |
| gldh | 0.61 | 0.28 | 0.742 | 1.18 | 0.330 | 0.17 | 0.825 | 1.44 | 0.267 | |
| alkphos | 0.62 | 9.96 | 0.002 | 0.59 | 0.557 | 0.28 | 0.744 | 0.78 | 0.469 | |
| ast | 0.84 | 3.53 | 0.039 | 1.99 | 0.155 | 2.00 | 0.153 | 1.21 | 0.327 | |
| gammagt | 0.81 | 0.62 | 0.578 | 0.43 | 0.696 | 3.27 | 0.051 | 1.35 | 0.285 | |
| bohbut | 0.86 | 7.12 | 0.003 | 2.32 | 0.112 | 0.30 | 0.798 | 0.73 | 0.528 | |
| ck | 0.53 | 2.08 | 0.170 | 0.50 | 0.576 | 2.21 | 0.156 | 1.42 | 0.272 | |
| mg | 1.00 | 10.25 | 0.000 | 0.97 | 0.423 | 0.19 | 0.905 | 1.60 | 0.216 | |
| ca | 1.00 | 8.33 | 0.001 | 0.57 | 0.639 | 0.70 | 0.560 | 3.29 | 0.038 | |
| phos | 0.62 | 7.26 | 0.007 | 1.87 | 0.190 | 0.55 | 0.576 | 0.21 | 0.797 | |
| caprat | 0.91 | 10.82 | 0.000 | 0.84 | 0.478 | 0.54 | 0.646 | 1.28 | 0.304 | |
| na | 0.88 | 1.80 | 0.182 | 0.64 | 0.581 | 0.51 | 0.656 | 2.16 | 0.129 | |
| k | 1.00 | 6.90 | 0.002 | 3.18 | 0.042 | 1.41 | 0.264 | 2.56 | 0.079 | * |
| cl | 1.00 | 56.98 | 0.000 | 11.20 | 0.000 | 0.08 | 0.970 | 1.92 | 0.153 | *** |
| bicarb | 0.64 | 4.66 | 0.028 | 2.18 | 0.149 | 0.51 | 0.601 | 0.20 | 0.808 | |
| angap | 0.94 | 0.56 | 0.634 | 4.41 | 0.015 | 0.66 | 0.578 | 0.23 | 0.864 | * |
| nakrat | 1.00 | 8.02 | 0.001 | 3.33 | 0.036 | 2.13 | 0.123 | 3.52 | 0.030 | * |
| rbc | 1.00 | 0.61 | 0.614 | 1.38 | 0.273 | 0.27 | 0.848 | 1.64 | 0.206 | |
| hb | 1.00 | 0.97 | 0.425 | 1.58 | 0.221 | 0.34 | 0.799 | 1.92 | 0.153 | |
| pcv | 1.00 | 0.38 | 0.768 | 1.49 | 0.243 | 0.46 | 0.712 | 1.06 | 0.384 | |
| mcv | 1.00 | 1.72 | 0.190 | 2.40 | 0.093 | 2.40 | 0.093 | 3.69 | 0.026 | |
| mch | 1.00 | 3.51 | 0.030 | 2.66 | 0.071 | 0.53 | 0.668 | 1.36 | 0.277 | |
| mchc | 1.00 | 4.61 | 0.011 | 0.45 | 0.719 | 1.83 | 0.170 | 6.61 | 0.002 | |
| wcc | 1.00 | 24.18 | 0.000 | 0.33 | 0.806 | 0.18 | 0.906 | 0.22 | 0.879 | |
| neut | 0.75 | 31.81 | 0.000 | 0.44 | 0.672 | 1.72 | 0.205 | 0.47 | 0.658 | |
| lymph | 1.00 | 1.31 | 0.294 | 0.30 | 0.827 | 2.20 | 0.114 | 0.40 | 0.757 | |
| mono | 1.00 | 5.48 | 0.005 | 0.80 | 0.505 | 0.97 | 0.425 | 0.30 | 0.824 | |
| eosin | 0.70 | 2.99 | 0.076 | 0.50 | 0.623 | 1.18 | 0.333 | 0.61 | 0.560 | |
| baso | 0.92 | 1.70 | 0.198 | 0.89 | 0.455 | 0.53 | 0.654 | 0.54 | 0.649 | |
| other | 0.48 | 1.03 | 0.363 | 1.03 | 0.363 | 0.97 | 0.378 | 0.97 | 0.378 | |
| rdw | 1.00 | 0.73 | 0.544 | 0.48 | 0.700 | 0.73 | 0.545 | 0.68 | 0.573 | |

Buffer and Electrolyte Experiments

These experiments investigated electrolyte concentrations during electrophoresis system treatments of whole blood. In addition the effect of different buffers (lactate and acetate-bicarbonate buffers) and variations to buffer concentration on whole blood by electrophoresis system treatment was studied.

Methods

Lactate buffer and various concentrations of Fresenius buffer were used in blood and plasma electrophoresis system runs. The electrophoresis system runs were sampled at 0, 5, 10, 15, 30, 45 and 60 minutes. Blood was centrifuged and the plasma analyzed for free hemoglobin. The blood plasma and plasma samples were assayed for electrolyte and glucose concentrations by the NATA accredited pathology laboratory.

Results

Electrolytes

Figure 26:
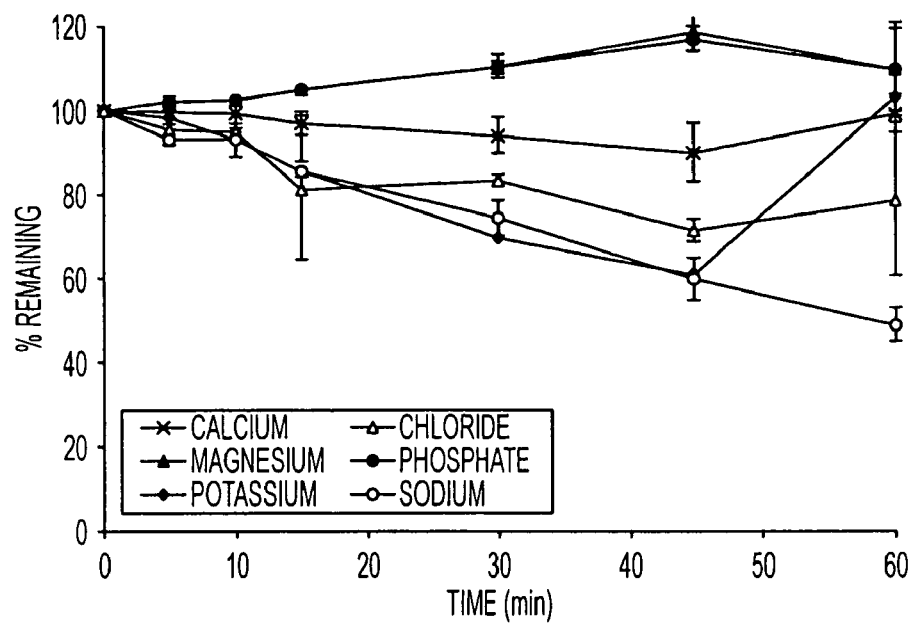
FIG. 26 shows removal of salt ions from heparinised blood when using 1× Fresenius buffer in an electrophoresis system according to the present claims at 80V.
Figure 27:
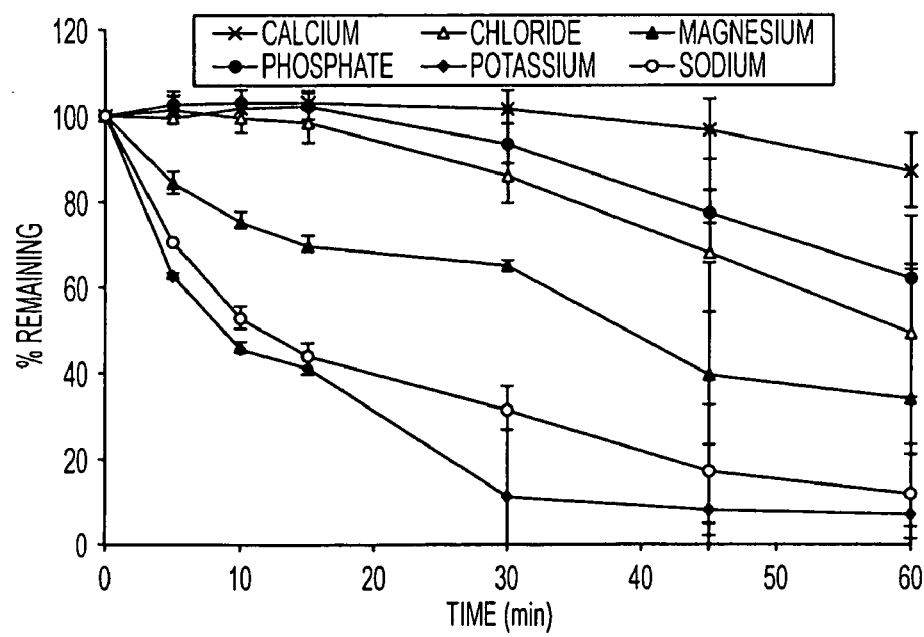
FIG. 27 shows removal of salt ions from heparinised plasma when using 1× Fresenius buffer in an electrophoresis system according to the present claims at 80V.
Figure 28:
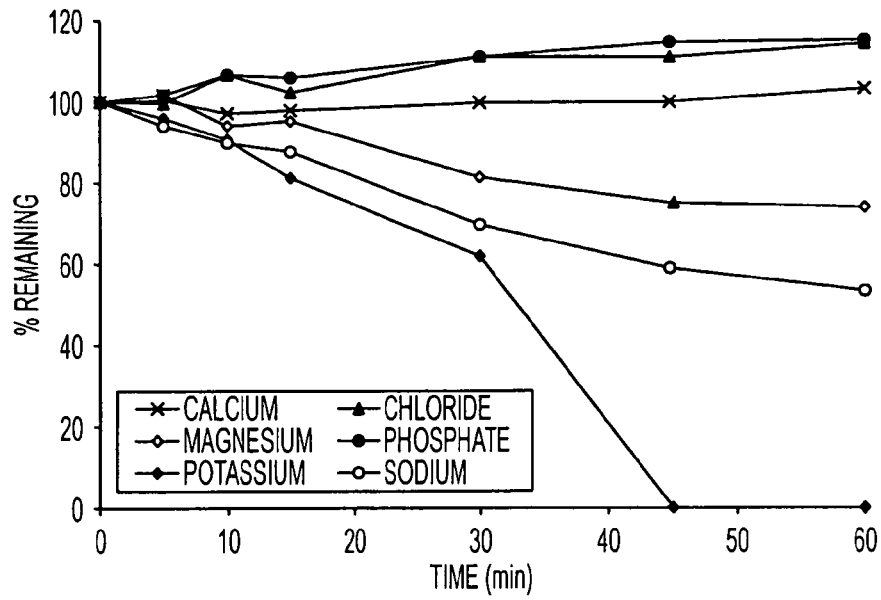
FIG. 28 shows removal of salt ions from heparinised blood when using slightly diluted Fresenius buffer in electrophoresis system according to the present claims at 80V; Fresenius buffer was diluted such that the Na+ concentration was reduced from 139.8 mM to 130 mM.

During the larger volume uremic waste removal experiments, electrolytes (calcium, chloride, magnesium, phosphate, potassium and sodium) concentrations were measured along with urea, creatinine and phosphate. Analysis of the electrolyte results found a trend suggesting that sodium and chloride concentrations increased above normal levels after blood was treated by the electrophoresis system (FIG. 26). However, the other electrolytes (calcium, magnesium, phosphate and potassium) concentrations decreased as blood was treated by the electrophoresis system. When treating plasma, all electrolyte levels decreased (FIG. 27). Comparing plasma to the whole blood electrolyte concentrations after treatment with the electrophoresis system suggest that the cellular component of blood may be affecting the sodium and chloride concentrations. To see whether the increase in sodium and chloride was buffer dependent, lactate buffer (Baxter PD dialysate) replaced the acetate-bicarbonate dialysate. When the buffer was changed, the same increase in sodium and chloride levels were observed (FIG. 28).

Figure 29:
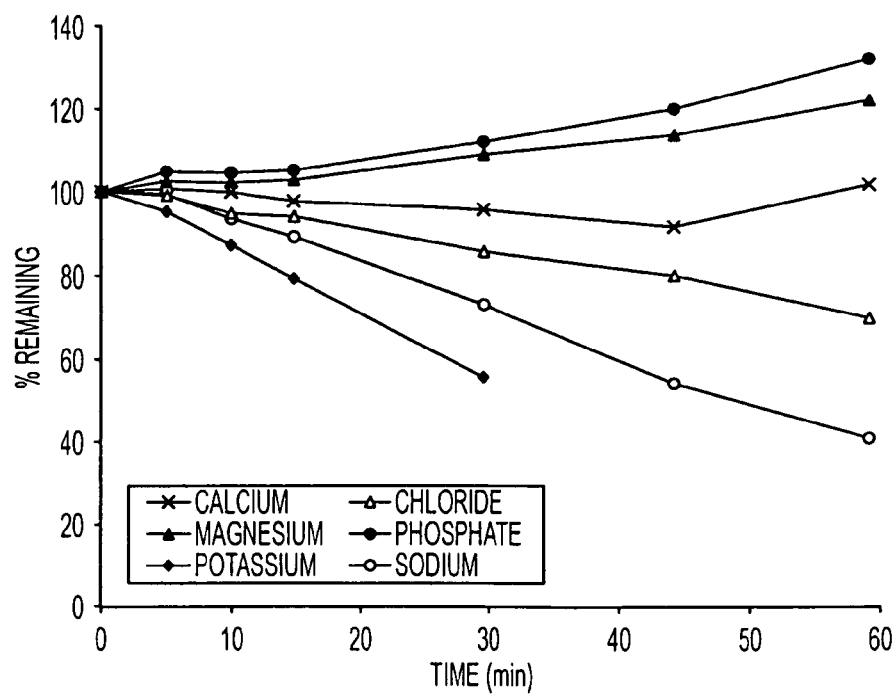
FIG. 29 shows removal of salt ions from heparinised blood when using Lactate peritoneal dialysis fluid in electrophoresis system according to the present claims at 80V.
Figure 30:
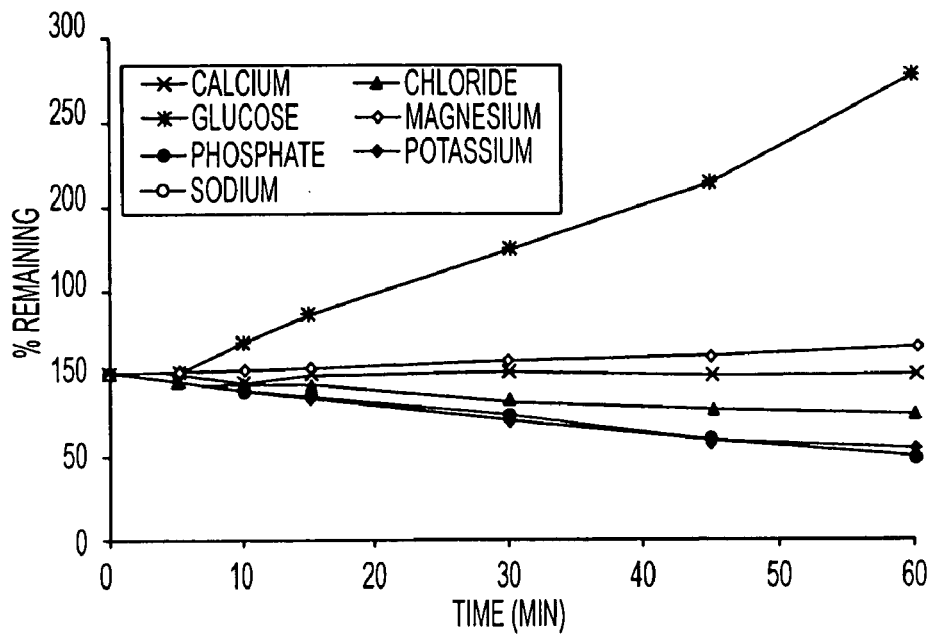
FIG. 30 shows removal of salt ions from heparinised blood when using ½× Fresenius buffer in electrophoresis system according to the present claims at 80V. Glucose was used to make up the osmolarity to the 1× Fresenius osmolarity of 296.1 mM.

To reduce the build up of sodium and chloride concentrations in blood after being treated by the electrophoresis system, the concentration of acetate-bicarbonate buffer was reduced. It was anticipated that by reducing the concentration of sodium chloride in the dialysate, its consequential build up would be reduced. By reducing the sodium concentration of the dialysate from 139.8 mM to 130 mM, only a minor change in sodium and chloride concentrations were observed after The electrophoresis system treatment (FIG. 29). A greater 1:1 dilution of the Fresenius dialysate with water was then tested for effect on sodium and chloride build up in the blood. To maintain the isotonicity of the 1:1 diluted dialysate, glucose was added to bring the osmolarity back to the original value. The use of the 1:1 dialysate resulted in a decrease in sodium and chloride accumulation in the blood after The electrophoresis system treatment (FIG. 30). However, this also resulted in a dramatic increase of glucose in the blood (FIG. 30).

Preliminary results indicated that reducing the salt concentration of the dialysate, and adjusting the isotonicity of the solution, improved the final sodium and chloride levels. Dialysate could be prepared by replacing excess sodium and chloride with other electrolytes which were found to be reduced during the treatment. Alternatively, electrolytes could be replaced with other non-ionic molecules which will maintain the isotonicity of the dialysate. Another alternative would be to change the current re-circulating dialysate system, to a single pass system.

Hemolysis

Figure 31:
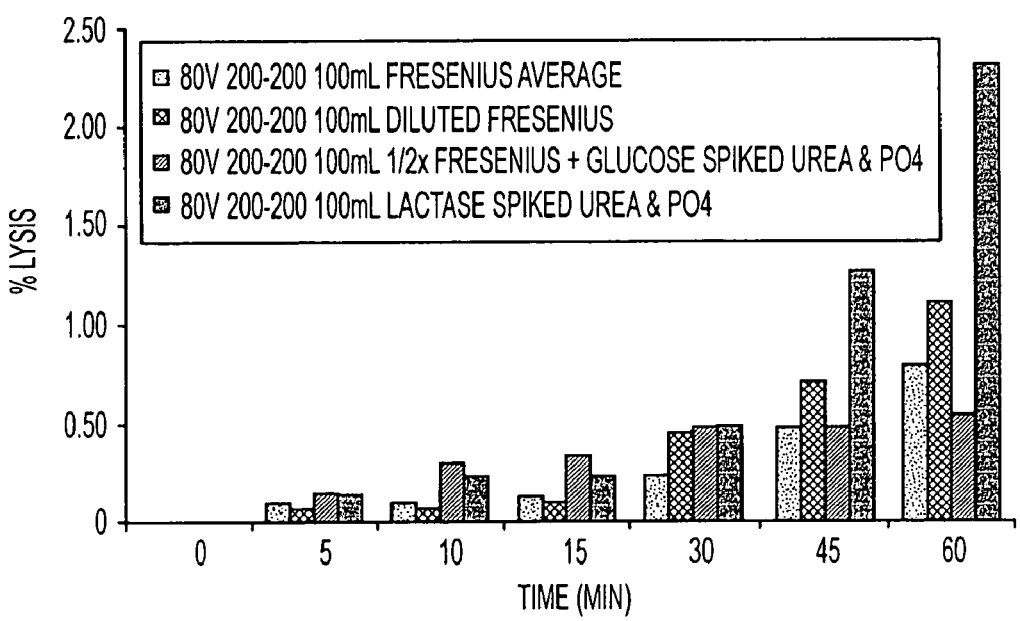
FIG. 31 shows effect of different buffers and buffer concentrations on hemolysis using electrophoresis system according to the present claims.

Because the concentration of salts present in the dialysate was being reduced by dilution, it was necessary to study the effect that this was having on hemolysis. These experiments suggest that slight dilution of Fresenius to reduce the sodium concentration from 139.8 mM to 130 mM ('diluted Fresenius') caused a slight but undesirable increase in the amount of lysis. Diluting Fresenius buffer 1:1 with water, and compensating with glucose to correct total osmolarity due to dilution, was shown to have a beneficial effect on hemolysis compared to full strength Fresenius at 80 volt potential. This may have been due to the fact that dilution of the Fresenius dialysate resulted in a lower conductivity and therefore a lower temperature rise when voltage was applied. Using lactate peritoneal dialysis fluid (Baxter) putatively increased hemolysis and hence may not and hence may not be an appropriate buffer to be used with The electrophoresis system for dialysis (FIG. 31).

Conclusion

From this data it could be suggested that not only does a lower conductivity buffer have beneficial effects on lysis, but also reduces salt pooling in the blood stream of sodium and chloride.

Other Uses For Electrophoresis System

Therapeutic uses in the treatment of other disease states which require the removal of toxic material from body fluids. Several options have been briefly described below.

Liver Dialysis

The mortality rate for liver failure is 80–90% with a rapid death (a week or two), without an effective liver transplant. During liver failure the build-up of toxic nitrogenous products (i.e. ammonia, trytophan, benzodiazepines, GABA, acetaminophen), foreign biological components, electrolytes and water imbalance within the body can cause serious damage. Current technologies are developing techniques to bridge the time until a suitable transplant can be identified. These technologies use a variety of filter types to remove the build up of excess molecules and toxins which have accumulated in blood. In renal dialysis applications The electrophoresis system has been shown capable of removing metabolic products, excess salts, selective protein removal and control fluid imbalances as well as being a biocompatible system. Therefore, the system according to the present claims may be incorporated in liver dialysis treatments, as an adjunct, to assist in increasing the bridge to finding a suitable liver transplant.

Cytokines

Inflammatory cytokines, such as IL-6, TNF$\alpha$ and IL-1 $\beta$, play a role in the pathogenesis of sepsis, shock and organ failure. It is unfavorable to remove all cytokines, but work has been conducted in reducing the excess amount of cytokine present in patients. One study used the application of therapeutic monoclonal antibodies to cytokines, soluble receptors and/or receptor antagonists have not resulted in any clinically significant outcomes. Another investigation involved using hemofiltration/hemodiafiltration to reduce the amount of cytokines present however they decided that the clinical relevance of their results needed further investigation. Preliminary data suggests the system according to the present invention has the potential to reduce/remove cytokines. The results from these experiments indicate that cytokine, such as IL-6, can be removed using the system according to the present invention.

General Discussion and Conclusion

This study established the use of membrane-based electrophoresis as a clinical medical device. In vitro and in vivo biocompatibility parameters such as coagulation, complement, hemolysis and preliminary cellular activation showed that treatment of blood and plasma by the claimed system and methods was a biocompatible process, for the biocompatibility parameters measured. During the animal study, the claimed procedures were well tolerated by the animals. There were no statistically significant adverse effects seen between the control and treatment groups for any biochemical or haematological value. In vitro analysis of molecule clearances showed that high charge to mass uremic toxins, such as phosphate, were efficiently removed by embodiments of the claimed system. While uremic toxins which had a low charge to mass ratio under physiological conditions, such as urea (neutral), were not removed as efficiently. Hence the removal of problematic uremic toxins, such as phosphate and charged middle molecule toxins are enhanced with the use of the electrophoresis system as an adjunct to existing technologies. Embodiments of the present claims can be combined with any of the existing medical technologies, including hemodialysis, hemofiltration, hemodialfiltration, REDY sorbent hemodialysis and/or even plasmapheresis.

Experiments determining the voltage which could be applied across blood suggest increasing electrical potential parameters resulted in a corresponding increase in hemolysis. The increase in hemolysis appeared to be related to the increased heat generated by the electrical potential, rather that the electrical potential itself.

Investigations into buffer composition indicate that reducing the salt concentration of dialysate, while maintaining an isotonic environment may be a possible alternative to using physiological salt solutions. Benefits of lower conductivity and salt concentrations include:

Reducing the sodium and chloride build up in the blood stream which was seen when physiological salt buffers were used.

Possible increase in transfer/removal rates with lower conductivity. The ability to increase the electrical potential may allow for the improved transfer rates of identified problematic uremic toxins.

Reduction in heat. Less heat generation results in less cell lysis and may allow for an increase in the maximum electrical potential which can be applied across the system.

Based on in vivo and in vitro investigations, other embodiments may also include:

An automated feedback mechanism controlling buffer conductivity;

An automated feedback mechanism controlling temperature;

In other embodiments, the heat exchanger may be modified to be made or coated with different biocompatible material such as metals (e.g., titanium) and polymers; in other embodiments, the entire heat exchanger system could be modified to suit the application by introducing different means to control temperature e.g., peltier cooling systems;

Other embodiments include modifications to the separation unit such as change the inlet and outlet ports to accommodate viscous biological fluids such as blood and plasma; modifying the cartridge to be less turbulent and angular; modify the grid structure to be thinner or incorporate different patterns to suit the biological fluid being processed; measures to reduce or control the effects of venous or arterial pressures on the cartridge; means to introduce anticoagulant in an automated fashion before the heat exchanger and/or the separation unit; use pumps or devices which direct or transport fluid and do not damage or lysis cells; appropriate monitors to measure fluid parameters, clearance levels and safety aspects during the treatment; buffers which incorporate a range of constituents to suit individual treatments; use buffers which enhance treatments; single or recirculating buffer systems, or a partial recirculating system; control fluid levels; the properties of different membranes to enhance treatments.

Electrically motivated dialysis according to the present claims use a fundamentally different motive force, namely an electric field, to remove contaminating solutes from patient blood. The use of an electric field for renal dialysis applications, or for the removal of uremic toxins from blood, has not been previously described in the literature. The removal of solutes and small proteins from patient blood according to the present claims depends on the electrophoretic mobility of the and small proteins, which is a function of the contaminating molecules charge to mass ratio. This basis for solute removal is different to previous modes of solute removal, which are based purely on the size or diffusive mobility of the contaminant molecule.

Along with the removal of select uremic toxins, embodiments of the present invention remove proteins known as middle molecules. A middle molecule that plagues long term renal dialysis patients is β2-microglobulin, which accumulates in the blood and then polymerises in bones and joints, with significant clinical consequences. In order to improve patient quality of life membrane-based electrophoresis was used in experiments to reduced β2-microglobulin.

Dialysis treatments not only needed to be able to remove waste metabolites and other problematic molecules, these treatment modalities needed to be safe for the patient. An important aspect of safety is the biocompatibility of the membrane materials and treatment system. The examples showed that membrane-based electrophoresis treatments had improved biocompatibility in the areas of coagulation and complement when compared to existing membrane types currently in clinical use. Similarly, there were no adverse effects of membrane-based electrophoresis processing on any of these standard biocompatibility measurements.

It will be appreciated by persons skilled in the art that numerous variations and/or modifications may be made to the specific embodiments without departing from the spirit or scope of the claims as broadly described. The present embodiments are, therefore, to be considered in all respects as illustrative and not restrictive.

The invention claimed is:

1. An electrophoresis system for removing or reducing concentration of a metabolic component from blood or plasma of a subject, comprising:
   (a) a first ion-permeable barrier having a defined pore size and pore size distribution disposed in an electric field area;
   (b) a second ion-permeable barrier having defined pore size and pore size distribution disposed between a cathode zone and the first barrier so as to define a treatment chamber therebetween;
   (c) means adapted for cooling blood or plasma from the subject;
   (d) means adapted to provide dialysate to the cathode zone and an anode zone;
   (e) means adapted to provide blood or plasma from the subject to the treatment chamber;

wherein, upon application of the electric potential, a metabolic component from the blood or plasma moves through at least one barrier into at least one of the cathode or anode zones, and wherein the barriers forming the treatment chamber are provided as a cartridge or cassette positioned between the electrode zones of the system.

2. The system according to claim 1 further including:
   (f) means adapted to return treated blood or plasma to the subject.

3. The system according to claim 1 wherein the first and second barriers have the same defined pore size and pore size distribution.

4. The system according to claim 1 wherein the first and second barriers have different defined pore size and pore size distribution.

5. The system according to claim 1 wherein the barriers are membrane hydrogels formed from polyacrylaminde.

6. The system according to claim 1 wherein the barriers of a defined pore size and pore size distribution which will not allow movement of serum albumin therethrough.

7. The system according to claim 1 wherein the barriers have a nominal molecular mass cut-off of less than about 60 kDa.

8. The system according to claim 1 further including a third ion-permeable barrier having a defined pore size and pore size distributions disposed in the electric field area forming a second treatment chamber.

9. The system according to claim 1 further including a third ion-permeable barrier having a defined pore size and pore size distributions disposed in the electric field area forming a plurality of treatment chambers.

10. The system according to claim 1 wherein the cartridge or cassette is removable from an electrophoresis apparatus adapted to contain or receive the cartridge.

11. The system according to claim 1 wherein the cooling means is selected from the group consisting of gas, liquid or solid heat transfer system or systems, cooled fluid jacket heat exchanger, and peltier cooler.

12. The system according to claim 11 wherein the cooling means is a gas, liquid or solid heat transfer system or systems.

13. The system according to claim 1 wherein the cathode zone and the anode zone are supplied with a dialysate or buffer solution.

14. The system according to claim 1 wherein the blood or plasma is supplied to the treatment chamber by a pumping means.

15. The system according to claim 1 wherein the electrode zones and the treatment chamber are configured to allow flow of the respective dialysate and blood/plasma to form streams therethrough.

16. A method for removing or reducing the concentration or amount of a metabolic component in blood or plasma of a subject, the method comprising:
(a) placing blood or plasma from the subject in a treatment chamber of an electrophoresis system comprising a first ion-permeable barrier having a defined pore size and pore size distribution disposed in an electric field area; a second ion-permeable barrier having a defined pore size and pore size distribution disposed between a cathode zone and the first barrier so as to define a treatment chamber therebetween; means adapted for cooling blood or plasma from the subject; means adapted to provide dialysate to the cathode zone and an anode zone; and means adapted to provide blood or plasma or plasma from the subject to the treatment chamber, wherein the barriers forming the treatment chamber are provided as a cartridge or cassette positioned between the electrode zones of the system;
(b) applying an electric potential between the cathode and anode zones causing movement of a metabolic component from the blood or plasma though a barrier into at least one of the electrode zones;
(c) maintaining step (b) until the desired amount of removal of the metabolic component from the blood or plasma is achieved; and
(d) returning the treated blood plasma in the treatment chamber to the subject, wherein the method substantially does not result in the blood or plasma being heated above physiological temperature of about 37° C.

17. The method according to claim 16 wherein the blood or plasma is passed through the cooling means of the electrophoresis system to reduce the temperature of the blood or plasma prior to being passed to the treatment chamber of the electrophoresis system.

18. The method according to claim 17 wherein the blood and plasma is warmed up to physiological temperature in the treatment chamber before being returned to the subject.

19. The method according to claim 16 wherein the subject is a renal dialysis patient.

20. The method according to claim 16 wherein the blood or plasma is preferably recirculated between the subject and the treatment chamber.

21. The method according to claim 16 wherein during electrophoresis cellular and biomolecular components of the blood or plasma are substantially retained in the treatment chamber, or if entering a barrier, being substantially prevented from entering the cathode or anode zones.

22. The method according to claim 16 wherein the metabolic components are selected from the group consisting of solutes, nitrogenous wastes, middle weight proteins, unwanted proteins and mixtures thereof.

23. The method according to claim 22 wherein the solutes are phosphates, the nitrogenous wastes are urea and uric acid, the middle weight proteins are beta-2microglobulin, and the unwanted proteins are autoantibodies.

24. The method according to claim 16 wherein the electric potential applied during the method does not substantially adversely affect cells or proteins present in blood or plasma.

25. The method according to claim 16 wherein flow rate of the blood or plasma to the treatment chamber is 20–1000 mL/min.

26. The method according to claim 16 wherein the electric potential is applied up to about 100 volts.

27. The method according to claim 16 wherein hemodialysis is carried out on the subject prior, subsequent to and/or in between applying the blood or plasma to the electrophoresis apparatus.

28. A method for removing or reducing concentration or amount of a metabolic component in blood or plasma of a patient, the method comprising:
(a) carrying out hemodialysis on blood or plasma of a patient; and
(b) subjecting the blood or plasma from the hemodialyzed patient to the method according to claim 16.

29. The electrophoresis system according to claim 1 for use in the dialysis of a renal patient.

30. The electrophoresis system according to claim 1, further comprising an artificial kidney, a plasma separating device, or an apheresis device to assist in the dialysis of a patient.

* * * * *